United States Patent [19]
Klippel et al.

[11] Patent Number: 6,043,062
[45] Date of Patent: Mar. 28, 2000

[54] CONSTITUTIVELY ACTIVE PHOSPHATIDYLINOSITOL 3-KINASE AND USES THEREOF

[75] Inventors: Anke Klippel, San Francisco; Lewis T. Williams, Tiburon, both of Calif.

[73] Assignee: The Regents of the University of California, Oakland, Calif.

[21] Appl. No.: 08/390,874

[22] Filed: Feb. 17, 1995

[51] Int. Cl.[7] .............................. C12N 9/12; C12N 15/54; C12P 9/00

[52] U.S. Cl. .............................. 435/131; 435/194; 435/6; 435/15; 435/975; 536/23.2

[58] Field of Search .................................... 435/194, 131, 435/6, 15, 975; 536/23.2

[56] References Cited

PUBLICATIONS

Hu, et al., "Ras–Dependent Induction of Cellular Responses by Constitutively Active Phosphatidylinositol–3 Kinase", *Science*, 268:100–102 (1995).

Dhand et al., "PI 3–kinase: structural and functional analysis of intersubunit interactions," *EMBO J.*, 13(3):511–521 (1994).

Escobedo et al., "cDNA Cloning of a Novel 85 kd Protein that has SH2 Domains and Regulates Binding of PI3–Kinase to the PDGF β–Receptor," *Cell*, 65:75–82 (1991).

Evan et al., "Isolation of Monoclonal Antibodies Specific for Human c–myc Proto–Oncogene Product," *Mol. Cell. Biol.*, 5(12):3610–3616 (1985).

Guan et al., "Eukaryotic Proteins Expressed in *Escherichio coli*: An Improved Thrombin Cleavage and Purification Procedure of Fusion Proteins with Glutathione S–Transferase," *Analyt. Biochemistry*, 192:262–267 (1991).

Hiles et al., "Phosphatidylinositol 3–Kinase: Structure and Expression of the 110 kd Catalytic Subunit," *Cell*, 70:419–429 (1992).

Hu et al., "Cloning of a Novel, Ubiquitously Expressed Human Phosphatidylinositol 3–Kinase and Identification of Its Binding Site on p85," *Mol. Cell. Biol.*, 13(12):7677–7688 (1993).

Hu et al., "Direct Association of p110β Phosphatidylinositol 3–Kinase with p85 is Mediated by an N–Terminal Fragment of p110β," *Mol. Cell. Biol.*, 14(4):2577–2583 (1994).

Klippel et al., "A Region of the 85–Kilodalton (kDa) Subunit of Phosphatidylinositol 3–Kinase Binds the 110–kDa Catalytic Subunit In Vivo," *Mol. Cell Biol.*, 13(9):5560–5566 (1993).

Klippel et al., "The Interaction of Small Domains between the Subunits of Phosphatidylinositol 3–Kinase Determines Enzyme Activity," *Mol. Cell. Biol.*, 14(4):2675–2685 (1994).

Matthias et al., "Eukaryotic Expression vectors for the analysis of mutant proteins," *Nucleic Acids Res.*, 17(15):6418 (1989).

Otsu et al., "Characterization of Two 85 kd Proteins That Associate with Receptor Tyrosine Kinases, Middle–T/pp60$^{c-src}$ Complexes, and PI3–Kinase," *Cell*, 65:91–104 (1991).

Skolnik et al., "Cloning of PI3 Kinase–Associated p85 Utilizing a Novel Method for Expression/Cloning of Target Proteins for Receptor Tyrosine Kinases," *Cell*, 65:83–90 (1991).

Wilson et al., "The Structure of an Antigenic Determinant in a Protein," *Cell*, 37:767–778 (1984).

*Primary Examiner*—Rebecca E. Prouty
*Attorney, Agent, or Firm*—Townsend and Townsend and Crew LLP; Karen B. Dow

[57] ABSTRACT

The invention provides a method of producing a constitutively active phosphatidylinositol 3-kinase (PI 3-kinase) comprising the catalytic p110 subunit covalently attached at the N-terminus to the iSH2 region of the regulatory subunit, p85. The invention discloses one form of the constitutively active kinase, p110*, which functions independently of growth factor stimulation. Expression vectors encoding a constitutively active PI 3-kinase and cells containing such expression vectors are provided. The invention also provides methods of using the constitutively active phosphatidylinositol 3-kinase to generate phosphoinositides, to identify cellular target proteins and associating molecules of PI 3-kinase, to screen for inhibitors of PI 3-kinase activity and to treat certain diseases, in particular, proliferative diseases. Kits comprising the constitutively active kinase are also provided.

15 Claims, 6 Drawing Sheets

CONSTITUTIVELY ACTIVE PHOSPHATIDYLINOSITOL 3-KINASE AND USES THEREOF

This invention was made with government support under Grant No. NIH RO1 HL32898, awarded by the Department of Health and Human Services. The government has certain rights in this invention.

BACKGROUND OF THE INVENTION

1. Field of the Invention

The present invention relates to molecules that participate in growth factor receptor signaling and cell proliferation. More particularly, the invention relates to a constitutively active phosphatidylinositol 3'-kinase, methods for its production, and diagnostic and therapeutic uses of the activated kinase and its derivatives.

2. Description of the Background Art

Growth factors play a role in embryonic development, cancer, atherosclerosis and the responses of tissues to injury. Growth factors are involved in several normal developmental processes as well as in pathological conditions.

One particular growth factor, platelet-derived growth factor (PDGF) is a major mitogen for mesenchymal cells, smooth muscle cells and glial cells. The binding of PDGF to its receptor (PDGF-R) triggers a diverse group of early cellular responses including activation of tyrosine kinases, stimulation of phosphatidylinositol turnover, alterations in ion fluxes, activation of phospholipase A2, changes in cell shape and the enhanced expression of a group of early response genes including the c-fos and c-myc proto-oncogenes.

In vivo, PDGF is stored in the α granules of blood platelets and does not circulate freely in blood. During blood clotting and platelet adhesion, the granules are released, often at sites of injured blood vessels, implicating PDGF in the repair of blood vessels. PDGF also stimulates migration of arterial smooth muscle cells from the medial to the intimal layer of the artery where they then proliferate as an early response to injury. Thus, activation of the PDGF-R receptor is involved in wound healing, in atherosclerosis, and in stimulating genes associated with cancerous transformation of cells, particularly c-myc and c-fos.

Because disregulation of the cellular processes involved in cell growth can have disastrous effects, it is important to understand and gain control over these processes. This requires identifying the participants in the signaling events that lead to mitogenesis and elucidating their mechanism of function. To this end, several cytoplasmic signalling molecules that mediate the mitogenic action of growth factor receptors, in particular, the PDGFR, have been identified and studied. One of these molecules is phosphatidylinositol 3-kinase.

Phosphatidylinositol 3-kinase is one of many activities stimulated by growth factors. Phosphatidylinositol 3-kinase is known to be involved in the regulation of cell growth and oncogenic transformation (Cantley et al., Cell, 64:1657 (1993)). The enzyme is found associated with receptor protein tyrosine kinases such as PDGF-R-β, CSF-1 receptor, Insulin receptor and IGF-1 receptor as well as non-receptor tyrosine kinase oncogenes, e.g., src, gag-abl and fyn. Studies on mutants of platelet-derived growth factor (PDGF) receptor have shown that phosphatidylinositol 3-kinase is a key mediator of PDGF-mediated mitogenic signaling (Fantl et al., Cell, 69:413 (1992); Valius et al., ibid., 73:321 (1993)). PDGF-R mutants that are unable to bind phosphatidylinositol 3-kinase are also unable to induce a mitogenic response after growth factor stimulation and unable to activate $p21^{c-ras}$ (ras). These data suggested that phosphatidylinositol 3-kinase acts upstream of ras in PDGF-stimulated signaling.

Until now, it has not been possible to examine the action of phosphatidylinositol 3-kinase directly, because the only known way of activating phosphatidylinositol 3-kinase involved the use of tyrosine kinases that are known to bind, phosphorylate and localize phosphatidylinositol 3-kinase. The use of receptor mutants to study signaling pathways has disadvantages, since several signaling molecules might share the same binding site on the receptor and it cannot be excluded that other signaling pathways are also affected by the mutation. Therefore it would be of importance to have a phosphatidylinositol 3-kinase molecule that functions independent of prior growth factor stimulation. The present invention satisfies this and other needs.

Phosphatidylinositol 3-kinase is a heterodimer consisting of a 110 kD catalytic subunit, p110 (the sequence for mouse p110 is hereby designated SEQ ID NO:11), and an 85 kD regulatory subunit, p85 (the sequence for mouse p85 is hereby designated SEQ ID NO:12). Upon growth factor receptor stimulation, the wild-type phosphatidylinositol 3-kinase is activated and can phosphorylate phosphatidylinositol at the 3' position of the inositol ring. Phosphatidylinositol 3-phosphates are candidate second messenger molecules. The catalytic subunit of phosphatidylinositol 3-kinase, p110, exhibits enzymatic activity in mammalian cells only when bound to the p85 subunit or to 102 amino acids of the p85 inter-SH2 (iSH2) region (Klippel et al., Mol. Cell. Biol., 14:2675–2685 (1994)). This iSH2 fragment bound to a region at the extreme N-terminus of p110 (Klippel et al., ibid., 14:2685 (1994)). Attempts to reconstitute a functional phosphatidylinositol 3-kinase in a cell-free system by mixing p85 expressed in E. coli with in vitro-translated p110 or by mixing the two subunits which had been separately expressed in COS cells or E. coli, have been less than successful.

SUMMARY OF THE INVENTION

The present invention constructs a constitutively active form of phosphatidylinositol 3-kinase that could be expressed in cells. This active phosphatidylinositol 3-kinase is advantageous in that it allows the activities of the enzyme to be studied directly and obviates the problems described. This constitutively active phosphatidylinositol 3-kinase that acts uncoupled from growth factor stimulation is useful in elucidating how phosphatidylinositol 3-kinase triggers cellular responses involved in the regulation of cell growth and provides novel approaches to the regulation or modulation of cell proliferation and therapeutic intervention in cancer.

In the present invention, a constitutively active phosphatidylinositol 3-kinase is produced by combining just the elements of p85 and p110 which are essential for activity, into a single molecule. This approach offers several advantages including that only one expression construct needs to be transfected into each cell. In addition, a single iSH2-p110 fusion molecule ensures a 1:1 stoichiometry of the active elements from each subunit.

A constitutively active p110 mutant, p110*, was constructed by attaching the p85 iSH2 region to the p110 N-terminal domain. Both domains were connected via a glycine-kinker that serves as a hinge region thereby giving the iSH2 domain more flexibility to interact with the p110 N-terminal domain. When expressed in mammalian cells p110* had reproducibly higher specific phosphatidylinositol 3-kinase activity than wildtype p110 coexpressed with iSH2. p110* also has protein-kinase activity. As with phosphatidylinositol 3-kinase activity, the protein-kinase activity is dependent upon the association of p110 with iSH2.

The invention provides a method of producing a constitutively active phosphatidylinositol 3-kinase by fusing the iSH2 domain sequences of the p85 subunit to the amino terminus of the p110 catalytic subunit using a linker, preferably glycine. p110 -p85iSH2 expression constructs and methods of preparing them, methods of expressing the fusion enzyme in cells, and isolation and purification of the constitutively active enzyme are disclosed.

This constitutively active phosphatidylinositol 3-kinase has various uses. One aspect of the invention relates to the use of p110* as a convenient and abundant source of active enzyme to generate inositol phosphate products in vitro. These products such as PI 3',4'-$P_2$, PI 3',4',5'-$P_3$ and PI 3'-P are commercially useful as reagents, particularly in studying lipid metabolism and signal transduction. The invention also provides kits containing the consitutively active phosphatidylinositol 3-kinase and other necessary reagents as well as instructions for use of the kinase in preparing inositol phosphate products.

The invention also provides methods for identifying target protein substrates that are phosphorylated by phosphatidylinositol 3-kinase, wherein the constitutively active phosphatidylinositol 3-kinase is contacted with cell lysates or libraries of test proteins in the presence of labeled ATP, and newly phosphorylated proteins are identified by comparing test cell lysates or test proteins with their respective negative controls. The negative control samples are subjected to the same reaction conditions except they are not contacted with the constitutively active phosphatidylinositol 3-kinase.

In another aspect of the invention, methods are provided for the isolation of proteins that associate with an active phosphatidylinositol 3-kinase. In one method, cells are transfected with an expression vector encoding the constitutively active kinase and the kinase-expressing cell is biosynthetically labeled in order to label the proteins. The cells are lysed under different detergent conditions and the constitutively active phosphatidylinositol 3-kinase is immunoprecipitated from the labeled cell lysate. Labeled proteins that co-immunoprecipitate with the active kinase are identified by SDS-PAGE followed by autoradiography.

A second method for isolating phosphatidylinositol 3-kinase associating proteins involves screening a phage or bacterial peptide library for peptides capable of binding to a constitutively active phosphatidylinositol 3-kinase preparation, and isolating any bound peptide by affinity purification.

Yet another approach to identifying associating proteins is by using the yeast two-hybrid system as described by Chien et al. *PNAS*, 88:9578–9582 (1991) and Kikuchi et al. *Mol Cell. Biol.*, 14:7483–7491 (1994).

The invention also provides methods of screening for antagonists of phosphatidylinositol 3-kinase activity and ras function. In an in vitro method, the constitutively active phosphatidylinositol 3-kinase is exposed to one or more test compounds and a substrate for phosphorylation, in a kinase reaction buffer containing [$^{32}$P]ATP to allow phosphorylation of the substrate. The enzyme can serve as its own substrate in a protein kinase assay while phosphoinositides are useful lipid substrates. The kinase activity is assessed by the presence and amount of the phosphorylated substrate. The absence of phosphorylated substrate is indicative that the test compound is an inhibitor of phosphatidylinositol 3-kinase activity.

In vivo, p110*-expressing cells can be exposed to small inhibitory substances added to the culture media and lack of cellular responses normally associated with the constitutively active kinase, noted.

Finally, the invention provides therapeutic formulations and methods of using these formulations to treat diseases. Proliferative diseases such as cancer can be treated by administering to the patient, a therapeutic formulation comprising an inhibitor of phosphatidylinositol 3-kinase activity in an amount effective to block the phosphatidylinositol 3-kinase activity in affected cells in the patient. A therapeutic formulation comprising a constitutively active phosphatidylinositol 3-kinase can be administered to a patient in a method to promote wound healing.

BRIEF DESCRIPTION OF THE DRAWINGS

FIG. 2A shows the detection of p110 molecules or the HA-tagged iSH2 fragment by immunoblotting. Molecular size markers are in kilodaltons. FIG. 2B shows the results of the assay for phosphatidylinositol 3-kinase activity as analyzed by thin-layer chromatography. In FIGS. 2B and C, the numbers above the lanes correspond to those of the samples shown in FIG. 2A. FIG. 2C shows the presence of phosphoprotein in the p110 immune complexes as visualized by autoradiography of the gel shown in FIG. 2A. The positions of phosphorylated p110, iSH2 and p110* are indicated by arrowheads.

FIG. 3A shows the effect of p110* on fos promoter activity. FIG. 3B shows the effect of wild-type phosphatidylinositol 3-kinase on fos promoter activity.

FIG. 5A shows ras·GTP levels determined as described. The ratio of ras·GTP/(ras·GDP+ras·GTP) was determined. In FIG. 5B, the activation state of downstream effectors of ras oocyte lysates were separated by SDS-PAGE and analyzed by immunoblotting with antibodies to raf or erk. In FIG. 5C, oocyte maturation was scored 24 hours postinjection and is shown as % germinal vesical breakdown (GVBD).

DESCRIPTION OF SPECIFIC EMBODIMENTS

Definitions

Figure 1:
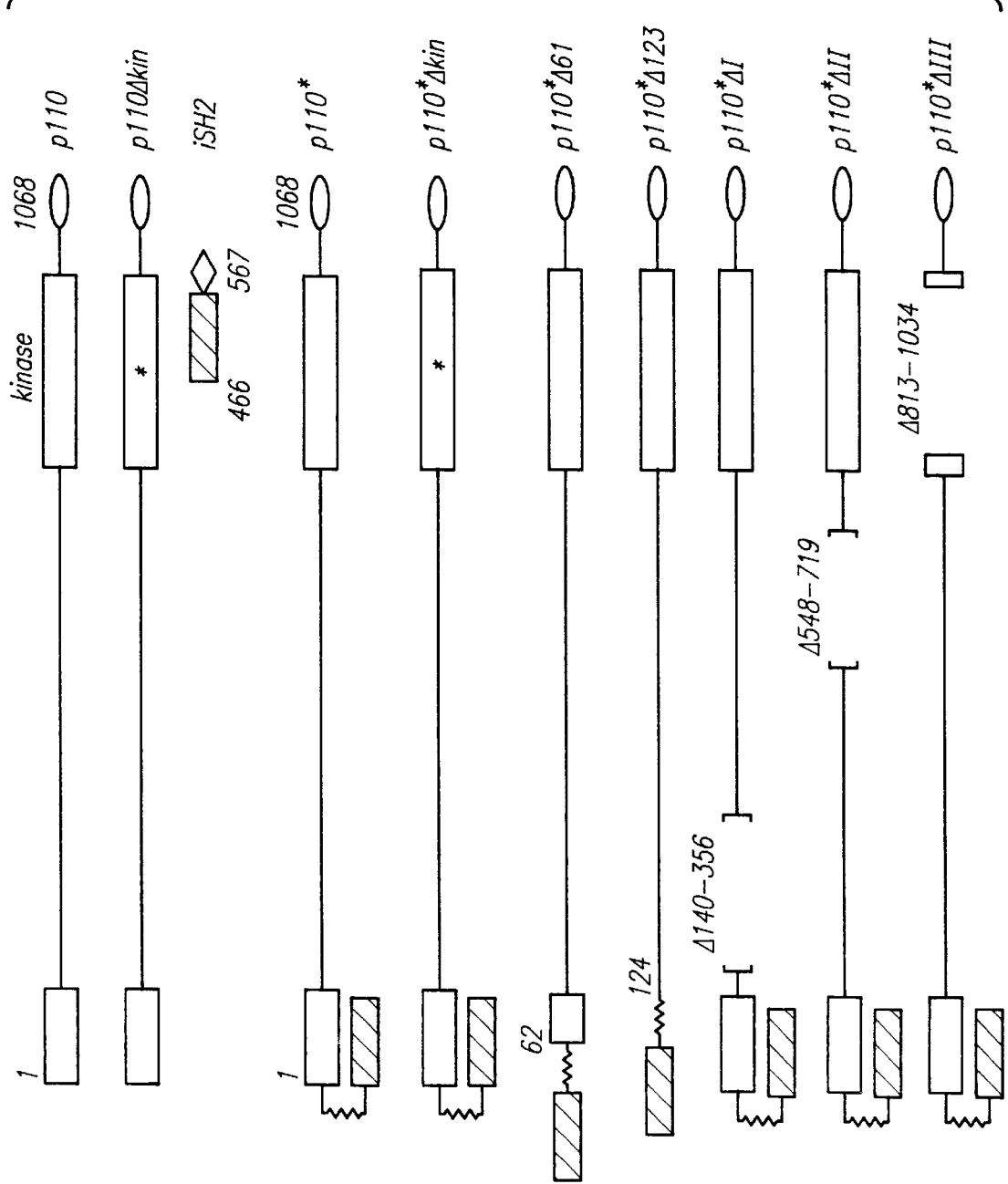
FIG. 1 is a schematic representation of the p85 and p110 derivatives constructed. The p110 constructs were tagged at the COOH-terminus with the myc epitope (oval); the iSH2 fragment of p85 contained a COOH-terminal influenza virus hemagglutinin (HA) epitope tag (diamond). The p110 region with similarity to the catalytic domain of protein kinases is depicted by a box labelled "kinase." The domain responsible for the interaction with the iSH2 domain of the p85 subunit is shown as a small box at the p110 $NH_2$-terminus. The p110Δkin protein is a kinase-deficient p110, in which the ATP-binding site was mutated as indicated by an asterisk within the catalytic domain. The iSH2 domain of p85 that is required for catalytic activity is represented by a hatched bar. The first and last amino acids of fragments are numbered with respect to their position in the wt p85 or p110 sequence. The p110* protein is a constitutively active chimera that contains the iSH2 domain of p85 fused to the $NH_2$-terminus of p110 via a flexible "glycine-kinker." p110*Δkin is the kinase deficient version of p110*. p110*Δ61 and p110*Δ123 lack 61 or 123 amino acids from the p110 $NH_2$-terminus, respectively, and can no longer associate with iSH2. p110*ΔI, p110*ΔII and p110*ΔIII are mutants that have internal deletions within the p110 structure as indicated.

Phosphatidylinositol 3-kinase is a heterodimer consisting of a 110 kD catalytic subunit, p110, and an 85 kD regulatory subunit, p85. The p85 subunit contains two SH2 domains, SH2-N and SH2-C. The region encompassing about 200 amino acids that separates these two SH2 domains is termed the inter-SH2 or "iSH2" region. The iSH2 region is defined by amino acids 434 to 599 of the p85 subunit, according to the amino acid position numbering in Klippel et al., *Mol. Cell. Biol.*, 13:5560 (1993).

"p110" refers to the wild-type catalytic subunit. The minimum region in p110 required for binding to iSH2 spans the first 123 amino acids at the N-terminus. The catalytic domain spans approximately amino acid 799 to 1068. For enzymatic activity, both the iSH2-binding region of 102 amino acids and the entire p110 region except the N-terminal 20 amino acids are required.

"p110*" refers to the constitutively active chimera that contains the iSH2 domain of p85 fused at its C-terminus to the N-terminus of p110 via a flexible "glycine-kinker." "Glycine kinker" herein refers to a glycine-rich sequence, composed of 7 glycines and other amino acids (depending on the restriction sites used). The minimal functional glycine-kinker hinge region used in this invention consists of Gly-Gly-Ile-Ser-Gly-Gly-Gly-Gly-Gly-Ile SEQ. ID NO. 2. Glycine as the smallest amino acid with no side chains is less likely than other amino acids to contribute to the formation of higher-order protein structures (secondary to quaternary) and is therefore best suited to compose a flexible hinge region. Flexible biomolecules like collagen fibers contain many glycine residues. Here the glycine kinker is used to link the C-terminus of the iSH2 to the N-terminus of the p110 subunit in such a way that the iSH2 region is flexible to interact with the p110 N-terminal region.

The amino acids of the polypeptides of the present invention are numbered with respect to their position in the wild-type p110 and p85 sequence according to Klippel et al., *Mol. Cell. Biol.*, 14:2685 (1994).

As used herein, "constitutively active phosphatidylinositol 3-kinase" means that the kinase is enzymatically active independent of prior growth factor stimulation and has high specific activity as both a phosphatidylinositol 3-kinase and as a protein kinase. Cells expressing the constitutively active kinase produced cellular responses normally only induced by growth factors, without prior activation by growth factors. Such cellular responses include induction of gene expression by fos-promoter activation, pp70 S6-kinase activation, membrane ruffling (in mammalian cells), *Xenopus laevis* oocyte maturation, activation of ras, raf, and MAP-kinase (in *Xenopus laevis* oocytes).

"Constitutively active phosphatidylinositol 3-kinase polypeptide" as used herein shall be deemed to include functional derivatives thereof or a homologs thereof of the iSH2 -p110 fusion protein. Derivatives produced by modifying any region in the present fusion construct including iSH2 and the p110 N-terminal and catalytic domain, by conservative amino acid substitutions are included. Thus, constitutively active phosphatidylinositol 3-kinase encompasses all derivatives of the present fusion p110* where the enzyme's constitutively active property is preserved.

A "linker" as used herein is defined as a short polypeptide that is recombinantly engineered into the fusion kinase to physically connect the iSH2 domain and the p110 subunit and produce one contiguous fusion polypeptide sequence while enabling the two subunits to interact. The linker sequence does not normally exist in either subunit.

Typically, the linker is positioned to connect the C-terminus of the iSH2 to the N-terminus of the p110 subunit. The linker can be 6 to 120 amino acids long, preferably, from 10–100 amino acids. Typically the linker will be composed of small, uncharged amino acids that provide flexibility so that the polypeptide can bend to allow the iSH2 and the p110 regions to interact without interfering with their functions. The linker can be composed almost entirely of one amino acid type such as the glycine kinker defined above, or it can be a combination of amino acids such as alternating glycine and alanine. Prolines would not be suitable to form flexible linkers. In a preferred embodiment, the linker is a glycine linker (also referred to herein as a glycine kinker), comprising about 7 glycine residues in a 10 amino acid polypeptide. A vector encoding such a glycine linker is disclosed in vector pGEX-KG (Guan et al., *Analyt. Biochemistry*, 192:262 (1991)).

Generally, the nomenclature used hereafter and the laboratory procedures in cell culture, molecular genetics, and nucleic acid chemistry described below are those well known and commonly employed in the art. Standard techniques such as described in Sambrook et al., *Molecular Cloning, A laboratory Manual*, 2nd edition, Cold Spring Harbor Laboratory, Cold Spring Harbor, N.Y. (1989), are used for recombinant nucleic acid methods, polynucleotide synthesis, cell culture, and transgene incorporation (e.g., electroporation, injection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

"Operably Linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The technique of "polymerase chain reaction," or "PCR," as used herein, generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands on the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See, generally, Mullis et al., *Cold Spring Harbor Symp. Quant. Biol.*, 51:263 (1987); Erlich, ed., *PCR Technology*, (Stockton Press, New York (1989)). As used herein, PCR is considered to be one, but not the only, example of a nucleic acid polymerase reaction method for amplifying a nucleic acid test sample, comprising the use of a known nucleic acid (DNA or RNA) as a primer.

By "substantially pure" is meant the object species is the predominant species present (i.e., on a molar basis it is more abundant than any other individual species in the composition), and not associated with normally found molecules. Preferably, a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally occurring.

As used herein, "substrate" of phosphatidylinositol 3-kinase refers to a molecule that the enzyme is capable of reacting with in vivo or in vitro and converting into a reaction product that is chemically different from the initial molecule. The substrate can be naturally occurring, synthetic, or recombinantly produced, and include lipids and proteins. The known enzymatic activity of phosphatidylinositol 3-kinase is the phosphorylation of inositol lipids as well as proteins. Therefore, typically, the lipid substrate for the phosphatidylinositol 3-kinase activity is a phosphoinositide such as phosphatidylinositol, phosphatidylinositol 4'-phosphate and phosphatidylinositol 4',5'-bisphosphate (PI 4',5'-P2). A protein substrate, also referred to herein as a target protein, applies to a protein that is phosphorylated by an active phosphatidylinositol 3-kinase enzyme on serine or threonine residues, in vivo or in vitro. Phosphatidylinositol 3-kinase is known to autophosphorylate in vitro and will phosphorylate the p85 subunit in vitro and in vivo. Thus, phosphatidylinositol 3-kinase substrates include both lipid and protein molecules and are not limited to the presently known substrates.

A phosphatidylinositol 3-kinase "associating molecule" or "interacting molecule" is one which has an affinity for the kinase and binds or physically interact with the kinase. The term "associating molecule" does not imply any particular molecular size or other structural or compositional feature other than that the molecule or compound in question is capable of binding or otherwise interacting with the kinase. This interaction can be transient, lasting only a fraction of a second or it can be stable so as to enable the detection of the complex of activated phosphatidylinositol 3-kinase associating molecule. The associating molecule may be a substrate of active phosphatidylinositol 3-kinase, an enzyme that phosphorylates the kinase, an effector molecule or a molecule that alters the conformation of phosphatidylinositol 3-kinase upon association. Associating proteins that can be investigated by this invention include but are not restricted to agonists and antagonists for cell membrane receptors, cellular proteins encoded by oncogenes or proto-oncogenes, lipids, toxins, hormones, sugars, cofactors, peptides, proteins, enzyme substrates, drugs and compounds from plant or animal sources.

The genes encoding the two subunits of phosphatidylinositol 3-kinase have been cloned from several species including bovine (Hiles et al., *Cell*, 70:419–429 (1992); Otsu et al., *Cell*, 65:91–104 (1991)), human p85 (Skolnik et al., *Cell*, 65:83–90 (1991), human p110β (Hu et al. *Mol. Cell. Biol.*, 13(12):7677–7688 (1993), mouse p85 (Escobedo et al., *Cell*, 65:75–82 (1991) and mouse p110 (Klippel et al., *Mol. Cell. Biol.*, 14:2685 (1994)). Therefore, a constitutively activated phosphatidylinositol 3-kinase can be produced using the genes from any of these species, following the same procedure as provided here and in the experimental examples.

Standard molecular biological and cloning procedures used herein, refer, e.g., to Sambrook et al. *Molecular Cloning, A Laboratory Manual*, 2nd edition, Cold Spring Harbor Laboratory, Cold Spring Harbor, N.Y. (1989).

Briefly, an expression vector is constructed to encode a constitutively active phosphatidylinositol 3-kinase polypeptide comprising the p85 iSH2 domain sequences linked at the C-terminus to the N-terminus of the entire p110 subunit, by a glycine linker. The iSH2 domain sequences consist essentially of amino acids 466 to 567. A myc epitope tag defined by the sequence EQKLISEEDL (SEQ ID NO. 1) is linked to the carboxy terminus of the p110 subunit.

The entire p110 subunit need not be used to construct the constitutively active phosphatidylinositol 3-kinase polypeptide. For example, the N-terminal 20 amino acids in p110 are not required for activity. Thus, a truncated constitutively active phosphatidylinositol 3-kinase polypeptide can be constructed without the first 20 amino acids of p110.

The entire p110 subunit or the N-terminal truncated version can be fused to the entire iSH2 domain of the p85 subunit or to a 102 amino acid segment of the iSH2 domain from amino acids 466 to 567 of the p85 subunit. A linker joins the C-terminus of the iSH2 domain sequences to the N-terminus of the p110 sequences. The linker is not restricted to a glycine linker and can be any suitable linker defined above.

Genomic or cDNA clones of the subunits can be used to prepare constructs encoding the fusion protein. Sequences encoding parts or all of a subunit, the glycine linker, as well as the tag can also be obtained by PCR off cDNA or genomic DNA, using the appropriate primers.

Preferably, the fusion polypeptide will contain a tag or label to enable the fusion kinase to be distinguished from the wild-type enzyme and to facilitate isolation and/or detection of the polypeptide. The tag is introduced into a site in the polypeptide that will not interfere with the folding and the function of the protein, generally at the N- or the C-terminus. The tag can be an epitope tag recognizable by an antibody, a member of a binding pair, an enzyme or any other suitable entity. The tag can be a cleavable sequence such as the phosphatidylinositol-glycan (PIG) signal sequence present in proteins such as alkaline phosphatase, DAF and acetylcholinesterase. The PIG sequence is cleavable by the enzyme phosphatidylinositol phospholipase C (PI-PLC) (Ferguson, *Ann. Rev. Biochem.*, 57:285–320 (1988)). The influenza virus hemagglutinin (HA) and the myc (10 amino acid—EQKLISEEDL) (SEQ ID NO. 1) epitopes are particularly useful tags. Examples of binding pairs are ligand-receptor, antigen-antibody and small molecules like avidin-biotin. Enzyme tags include horse radish peroxidase, alkaline phosphatase and β-galactosidase which can act on a substrate to produce a color signal. The tag can be at the N-terminus of the iSH2 domain, the C-terminus of p110, or in between the iSH2 and p110. In a preferred embodiment, the iSH2-p110 fusion protein is tagged at the C-terminus of p110 with a 10 amino acid myc epitope—EQKLISEEDL (SEQ ID NO. 1) (Klippel et al., *Mol. Cell. Biol.*, 13:5560–5561 (1993)).

The invention provides expression vectors encoding these constitutively activated phosphatidylinositol 3-kinase polypeptides. The constitutively activated phosphatidylinositol 3-kinase or its derivatives may be produced in prokaryotes, although eukaryotic systems are preferred. The protein can also be expressed in insect cells, e.g., in the Sf9 cell line, using baculovirus vectors, as well as in yeast. Suitable vectors include plasmids, viral, YAC.

Preferably, the chimeric kinase is produced in mammalian cells. A variety of expression vectors compatible with the mammalian cell host can be used, e.g., pCG. The expression vectors will contain the necessary elements for transcription and translation of the DNA fragments into polypeptide if these elements are not already present in the DNA fragments themselves. These necessary elements include a promoter 5' of the DNA insert to be expressed, a transcription and translation initiation site, stop codons, poly-A signal sequence, splice signals. DNA sequences encoding the fusion protein will be operably linked to a promoter appropriate for expression in a particular cell type. Usually a strong promoter will be employed to provide for high level transcription and expression. Examples of strong promoters include human cytomegalovirus promoter, SRα and retroviral LTRS. An enhancer may be necessary to function in conjunction with the promoter. Inducible promoters are also contemplated.

The vector may also include selectable markers for selection in both the bacterial host when amplifying the plasmid, and the eukaryotic host where the protein is expressed. Such selectable markers are well known in the art. Alternatively, selectable markers may be provided on a separate vector which cab be co-transfected with the kinase-encoding expression vector. The vectors may also include sequences encoding tagging moieties to be covalently linked to the fusion kinase-encoding fragment at the desired terminus of the fragment.

In a preferred embodiment, the DNA fragments encoding iSH2 -p110 are cloned into the mammalian expression vector pCG which contains the human cytomegalovirus enhancer/promoter region and the translation initiation region of the herpes simplex virus thymidine kinase gene. This modified pCG plasmid vector also contains sequences encoding the 10 amino acid myc epitope which is fused to the C-terminus of p110.

Since wild-type phosphatidylinositol 3-kinase appears to be ubiquitous in expression, the fusion enzyme can be expressed in most mammalian cell type. Cells that are amenable to transfection and in vitro cell culture manipulation are preferred. In a specific embodiment, mammalian fibroblast cell lines such as COS-7, NIH 3T3 and rat 3YI are transfected with the expression vectors encoding the fusion kinase. Smooth muscle cells, Chinese hamster ovary (CHO) cells, 293 cells (human embryonic kidney), tumor cells and generally cells capable of proliferation are contemplated.

The invention also provides methods of producing a constitutively active phosphatidylinositol 3-kinase. The DNA expression vectors encoding the active fusion kinase polypeptide are introduced into the appropriate cellular host under conditions which favor expression of the polypeptide and isolation of the resultant expressed polypeptide. This implies using an expression vector compatible with the host cell, the vector containing the necessary elements described above for expression of the polypeptide. The tranfected cells are then provided with the optimum nutrient, gas and temperature conditions for optimal protein production. These conditions will depend on the cell type.

Standard methods such as transfection, electroporation and microinjection can be used to introduce the expression vector into the host cell. Transient or stable transfection procedures can be used. In the present invention, the fibroblast cells are transiently transfected using DEAE-dextran and stably transfected by lipofection, calcium phosphate precipitation of electroporation.

For certain studies such as in identifying associating proteins and effectors in vivo, the fusion kinase can be isolated from an expressing cell and introduced into a second cell by microinjection. This approach can be used especially if the second cell under study is not amenable to transfection. The fusion kinase should be isolated under conditions that prevent or minimize degradation or inactivation of the kinase. See, e.g., Harris, et al., "Protein Purification Applications," IRL Press, Oxford University Press, 1989; and Deutscher, "Methods in Enzymology: Guide to Protein Purification," Vol. 182, Academic Press, Inc., 1990.

While immunoprecipitates of the fusion kinase might be adequate for performing kinase assays, certain applications may require the protein to be provided in substantially pure form. A substantially pure form of the fusion kinase can be prepared by contacting the lysates from transfectants over a solid matrix such as an bead affinity column containing, an immobilized moiety that binds the tag on the fusion protein. If the tag is an epitope, the moiety on the matrix is typically an antibody. Depending on the nature of the tag, receptors or ligands of the tag are also suitable for capturing the fusion kinase. The fusion kinase can also be purified over an affinity column using an antibody to the kinase itself and eluted with peptides.

The invention also provides a readily available and abundant source of activated phosphatidylinositol 3-kinase enzyme to generate inositolphosphate products (also called phosphoinositides) in vitro from phosphatidylinositol lipid substrates. The reaction products of phosphatidylinositol 3-kinase activity include phosphatidylinositol 3'-phosphate (PI 3'-P or PIP) which is generated from the substrate phophatidylinositol (PI); phosphatidylinositol 3',4'-bisphosphate (PI 3',4'-$P_2$) generated from the phosphorylation of the substrate phosphatidylinositol 4'-phosphate (PI 4'-P); and phosphatidylinositol 3',4',5'-trisphosphate (PI 3',4',5'-$P_3$) derived from phosphatidylinositol 4',5'-bisphosphate (PI 4',5'-$P_2$).

These products of phosphatidylinositol 3-kinase are commercially useful reagents, for example, to study inositol metabolism, to study the role of such lipids as second messengers in transmembrane signaling and the effectors of these lipids, as well as in pharmacological studies. These reagents are also suitable for use as standards or markers, e.g., on thin layer chromatograms to identify the species of phospholipid from a kinase reaction.

Inositol phosphates are not efficiently produced synthetically and heretofore, were not available commercially because of difficulty in obtaining sufficient active phosphatidylinositol 3-kinase enzyme. For example, the chemical synthesis of PI 3'-P is laborious and involves isomerization of PI 4'-P. The yield is approximately 8% PI 3'-P, which is about 80% homogenous after TLC-based purification (Walsh et al., PNAS 88, pp. 9184–9187 (1991)). The use of TLC for purification limits the amount of product that can be produced at one time. Furthermore, it is unclear how PI 3',4'-$P_2$ or PI 3',4',5'-$P_3$ are synthesized from the limited source of PI 3'-P.

However, using a reusable column of immobilized constitutively active phosphatidylinositol 3'-kinase, defined PI 3'-P, PI 3',4'-$P_2$ or PI 3',4',5'-$P_3$ derivatives can be generated simply by the selective use of the appropriate substrate. As pointed out, the enzymatic activity of wild-type phosphatidylinositol 3-kinase is dependent on growth factor activation of the cell and the association of the catalytic p110 subunit with p85. The present availability of large amounts of recombinantly produced, constitutively active phosphatidylinositol 3-kinase makes it possible to efficiently prepare inositol phosphate reagents on a commercial scale.

The appropriate kinase reaction conditions for preparing these products enzymatically using phosphatidylinositol 3-kinase have been previously described (see, Whitman and Cantley, Nature, 332:644 (1988)). The reagents required are: 30 mM Hepes pH 7.4; 20 mM $MgCl_2$; 200 µM adenosine; varying concentrations of phosphoinositide substrate and of ATP. The phosphoinositide products can be prepared prelabeled by including for, e.g., [$\gamma^{32}$P]ATP in the reaction mixture or using [$^3$H]- or [$^{14}$C]- initial substrates. These products are then purified from the reaction mix by thin layer chromatography (TLC).

Kits containing reagents for preparing the inositol phosphate products are also provided by this invention. The kit can have different compartments to hold each reagent. The contents of the kit will include reagents and instructions for the use of the reagents to prepare inositol phosphate products. One of the reagents will be at least one aliquot of a preparation of the constitutively active phosphatidylinositol 3-kinase. The aliquots can be contained in any suitable container such as a vial or a tube. The phosphatidylinositol 3-kinase can be provided in solution or in lyophilized form, and may be immobilized. The kinase preparation may also contain in it preservatives such as sodium azide or protease inhibitors such as EDTA. A carrier protein such as BSA or ovalbumin, usually between 0.5–5%, may be included to stabilize the kinase. The solution form of the kinase may contain up to 50% glycerol if the enzyme is to be stored frozen at −20° C. to −70° C. If the kinase is provided in lyophilized form, the kit can include a reconstitution buffer to reconstitute the enzyme, as well as a reaction buffer. Alternatively, the phosphatidylinositol 3-kinase enzyme can be added to the kinase reaction buffer and the solution freeze dried. This form can be readily reconstituted in distilled water with the necessary salt components for the kinase reaction already present so that no additional reaction buffer need be supplied. Thus, depending on the form and composition of the kinase preparation, different buffers may be included in the kit and they may be provided in more than one aliquot. These buffers are, of course, optional.

Another reagent that may be supplied in the kit is ATP, preferably in dried form. One or more substrates for the reaction can also be provided. The phosphoinositide substrates include PI, PI 4'-P and PI 4',5'-$P_2$.

In addition to its lipid (phosphatidylinositol 3) kinase activity, phosphatidylinositol 3-kinase also has protein kinase activity. The purified p110* is useful for identifying in vitro and in vivo cellular target protein substrates. As used herein, target protein substrate or protein substrate refers to a protein that is phosphorylated by an active phosphatidylinositol 3-kinase enzyme on serine or threonine residues, in vivo or in vitro.

To identify a target protein in vitro, a kinase assay can be carried out wherein the p110* kinase or its derivatives is contacted with a cell lysate, a test protein or a library of proteins under conditions which allow the phosphorylation of the proteins. The p110* kinase can be provided in the assay in substantially purified form or as an immunoprecipitate. The substantially purified p110* can be added to the kinase reaction as soluble enzyme or it can be immobilized on a solid matrix. Using immobilized p110* facilitates separation and isolation of the target protein substrate from the reaction.

The solid matrix can be a plastic surface such as a microtiter plate well, a membrane, or typical column matrices such as agarose or sepharose beads. The immobilization can be indirect, through the use of a second moiety such as an antibody, that is directly attached to the matrix. The lysate or solution of test protein will then be applied over the immobilized p110*.

The test protein or proteins can also be provided displayed on a phage. Screening of phage display libraries for ligands and substrates are known in the art (see, e.g., Schatz, Bio/Technology, 11:1138–1143 (1993)). Phage display libraries allow the testing of at least $10^7$ different peptide sequences for potential substrates or interacting peptides. More conveniently, the test protein is present in a test cell lysate or an extract from a cell.

Lysates can be prepared from any cell that expresses endogenous phosphatidylinositol 3-kinase or from a phosphatidylinositol 3-kinase transfectant. The cells can be stimulated prior to lysis. Cultured cell lines as well as cells freshly isolated from a mammal can be used. Preferably, lysates are prepared from mammalian cells of mesenchymal origin, smooth muscle cell, B and T cell. Fibroblast cell lines such as COS or NIH 3T3 cells are commonly used.

Certain cellular events along the signaling pathway may be necessary to produce the substrate, release it from sequestration, expose the phosphorylation site on the substrate or modify the substrate in some other manner that will make it accessible to and reactive with phosphatidylinositol 3-kinase. In such instances, it may be necessary to add p110* to stimulated cell lysates. Cells expressing the appropriate surface receptors can be stimulated with the normal corresponding ligand or with an antibody to the receptor. For example, fibroblasts expressing PDGF-R can be stimulated with the growth factor, PDGF; B and T cells can be activated through their respective B and T cell receptors with antigen or receptor-specific antibodies. Other activation reagents such as phorbol esters, that do not stimulate through surface receptors, can also be used. The cells can be stimulated for various lengths of time, typically 30 seconds to 1 hour, to study the kinetics of the protein substrate. Phosphatase inhibitors such as sodium vanadate or sodium pyrophosphate may be included in the lysis buffer to prevent dephosphorylation especially of p110* substrates in the lysate after reacting with the kinase. A lysate sample not contacted with p110* will serve as a negative control lysate.

The kinase and test protein or test cell lysate are contacted in a kinase reaction performed in a kinase buffer containing ATP, typically radiolabeled ATP, e.g., [$\gamma^{32}$P]-ATP. Upon completion of the kinase reaction, the test protein sample or test lysate is compared with its respective negative control to detect any phosphorylated target protein present in the test cell or phosphorylated test protein. Any phosphorylated target protein can be detected by the presence of $^{32}$p on the protein if [$^{32}$P]-ATP is used.

Following the kinase reaction, the reactants of the kinase assay are typically separated by SDS-PAGE, and target proteins detected by autoradiography of the gel. Sample lanes corresponding to test lysates are compared with that of the negative control to detect any radiolabeled bands unique to the test lysates. Such bands indicate putative proteins phosphorylated by the fusion phosphatidylinositol 3-kinase. The apparent molecular weight of such bands are determined by comparing with standard molecular weights on the gel.

The electrophoresed proteins can also be transferred onto a membrane and autoradiography and/or Western blotting performed on the membrane. Nylon or nitrocellulose membranes are useful matrices for blotting. The kinase reaction need not use radiolabeled ATP if for the immunoblotting, antibodies that specifically bind phosphoserine or phosphothreonine are available and are used to detect bands corresponding to phosphorylated proteins and to determine the specificity of phosphorylation.

The target phosphorylated protein can be isolated from a gel by excising the protein band from the gel and eluting the protein off the gel slice. Alternatively, the phosphorylated target protein can be isolated by affinity purification directly from the reaction mix, using an immobilized receptor specific for a phosphorylated product. Suitable receptors are antibodies that specifically recognize and bind phosphoserine or phosphothreonine residues. The target protein is eluted from the column, e.g., using free phosphotyrosine in the case of a tyrosine phosphoprotein.

The identity of the isolated target protein can be determined by immunoblotting with a combination of specific antibodies. From the migration of the protein on SDS-PAGE, the apparent molecular weight can be determined. The target protein can also be identified after metabolic labeling of cells expressing the constitutively active phosphatidylinositol 3'-kinase with orthophosphate. Cell lysates can then be separated by 2-D electrophoresis and compared to the pattern obtained with nonexpressing cells by autoradiography.

The phosphorylated amino acid can be determined by acid digestion of the 32P-labeled protein and separation of the resultant amino acids by thin layer chromatography. The migration of the labeled amino acid is compared with radiolabeled standards of phosphoserine and phosphothreonine (Dadassi et al., *J. Biol. Chem.*, 265:20996 (1990)).

The amino acid sequence can be obtained by microsequencing the isolated protein. Sequences obtained can be used to search a sequence databank which may help identify the protein or provide known sequence homologs. Using the amino acid sequence, peptides can be designed and synthesized. The isolated protein or its peptide derivatives are useful to generate monoclonal and polyclonal antibodies following standard techniques as described in Ed Harlow and David Lane, *Antibodies A laboratory Manual*, Cold Spring Harbor Laboratory, Cold Spring Harbor, N.Y. (1988). These antibodies are useful reagents for: isolating more of the target protein from cells for further protein characterization; immunocytochemistry and immunoblotting; and blocking growth factor activated signaling, amongst other things.

Antibodies are produced by immunizing an appropriate vertebrate host, e.g., mouse, with the peptide itself, or in conjunction with a conventional adjuvant. Usually two or more immunizations will be involved, and the blood or spleen will be harvested a few days after the last injection.

For polyclonal antisera, the immunoglobulins may be precipitated, isolated and purified, including affinity purification. For monoclonal antibodies, the spenocytes normally will be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570 and 4,618, 577.

From the amino acid sequence, degenerate DNA probes can be synthesized for probing genomic or cDNA libraries to isolate the gene encoding the target protein.

One approach to understanding the role of wild-type phosphatidylinositol 3-kinase in cell proliferation and oncogenesis is to identify proteins that associate or interact with the constitutively active enzyme. The present invention provides methods for identifying phosphatidylinositol 3-kinase associating molecules. Lipid or protein substrates will invariably associate with the kinase, although the association may be transient. This section will address associating molecules other than the lipid and protein substrates already described above.

Phosphatidylinositol 3-kinase associating molecules can be identified as follows. The constitutively active enzyme is expressed in cells as described above. Cells expressing the fusion enzyme are identified and biosynthetically labeled for eg. using [$^{35}$S]-met [$^{125}$] or [$^{32}$P]ATP. Methods for biosynthetic labeling of proteins are well known. [$\gamma^{32}$P]ATP will specifically label phosphorylated proteins. The in vivo labeled cells are lysed and the constitutively active kinase immunoprecipitated from the lysates via its tag, to form an immunocomplex. Different detergents and detergent concentrations should be tested to optimize stabilizing the associating complex. Typically, detergents such as Deoxycholate, NP40, and digitonin are used in the range of 0.1–2%. Other suitable detergents include octylglucopyranoside and derivatives, Chaps/Chapso, and Tween 20. Immunoprecipitating a nonrelated protein or a different kinase, a mutant phosphatidylinositol 3-kinase, or using a nonspecific antibody provide suitable negative controls. The immunocomplex is solubilized to release the labeled immunoprecipitated proteins contained therein. Any protein that specifically co-immunoprecipitates with the constitutively active phosphatidylinositol 3-kinase polypeptide and is present in the immunocomplex is detected by a combination of SDS-PAGE of the solubilized immunocomplexes, and autoradiography to look for labeled proteins specific to p110* immunoprecipitated samples. Western blots can be prepared and autoradiography performed on the blots. Any protein that co-immunoprecipitates with the kinase is considered an associating protein. The associating protein can be characterized as described above for the target protein substrate.

Alternatively, peptide libraries can be screened for binding to the immobilized active enzyme. Fodor et al. in U.S.

Pat. No. 5,143,854 describe methods of preparing arrays of peptides on a solid matrix, screening of the peptides and automated detection of peptides bound to ligand. The constitutively active phosphatidylinositol 3-kinase polypeptide can be provided in substantially pure form, immobilized directly or indirectly onto a solid matrix. The enzyme can also be provided as an immunocomplex containing the enzyme bound to an antibody that specifically recognizes the tag on the enzyme. The tag antibody can be covalently bound to a solid matrix such as protein A-sepharose beads or directly conjugated to plain sepharose beads. Phage or bacterial peptide libraries are exposed to a constitutively active phosphatidylinositol 3-kinase to allow one or more peptides to bind to the enzyme. Peptides which bind the enzyme are considered associated proteins and can be isolated by affinity purification.

Yet another approach to identifying associating proteins is by using the yeast two-hybrid system as described by Chien et al., *PNAS,* 88:9578–9582 (1991) and Kikuchi et al., *Mol Cell. Biol.,* 14:7483–7491 (1994). Basically, this system involves expressing two hybrid proteins in a yeast cell. Plasmids encoding the two hybrid proteins are constructed. One hybrid consists of the DNA-binding domain of the yeast transcriptional activator protein, GAL4, fused to the known protein; the other hybrid consists of the GAL4 activation domain fused to protein sequences encoded by a library of genomic or cDNA fragments. Interaction between the known protein and a protein encoded by one of the library plasmids leads to transcriptional activation of a reporter gene containing a binding site for GAL4. This method can be applied here by constructing the first hybrid as GAL4-p110*. Other suitable hybrid proteins include LexA-p110*. The two plasmids encoding separate hybrid proteins are then introduced into yeast. Transcriptional activation of the reporter gene, typically β-gal, is easily assayed following standard procedures as described in Chien or Kikuchi, above.

The constitutively active phosphatidylinositol 3-kinase may be useful as therapeutic formulations to promote wound healing and tissue regeneration in a patient.

Inhibitors or antagonists of phosphatidylinositol 3-kinase activity are useful in modulating or blocking signal transduction through the PDGF receptor (PDGF-R) and events downstream of phosphatidylinositol 3-kinase activity such as the activity of the ras oncogene or the transcription of early genes such as fos and myc which are associated with cancerous transformation of cells. The ability to block these activities is useful in therapeutically treating proliferative diseases such as cancer and psoriasis, as well as in treating viral, inflammatory, allergic and cardiovascular diseases, e.g., atherosclerosis.

Thus, one aspect of the invention relates to a method of screening for inhibitors or antagonists of phosphatidylinositol 3-kinase activity. A method of using a phosphatidylinositol 3-kinase inhibitor in a therapeutic formulation to treat proliferative diseases as well as the formulations comprising these inhibitors, are also provided.

As used herein, a compound or substance is an "inhibitor" or "antagonist" of phosphatidylinositol 3-kinase if the constitutively active kinase shows no or significantly reduced enzymatic activity in the presence of the compound as compared to its absence. The loss or reduction of one or both of the phosphatidylinositol 3- or the protein kinase enzymatic activity is considered an inhibition effect. The inhibition of the enzymatic activity of a constitutively active phosphatidylinositol 3-kinase can be tested in an in vitro kinase assay by exposing the kinase to one or more test compounds in the presence of [$^{32}$]ATP and a substrate as described above, and the presence of phosphorylated substrate determined. For example, the p110* can be provided in substantially purified form in solution or immobilized or immunoprecipitates of the active enzyme can be used. The substrate can be a lipid such as a phosphoinositide. For protein kinase activity, p110* itself can serve as substrate.

Methods of detecting both kinds of substrates have been described above. The absence or reduced amount of a phosphorylated substrate is indicative that the test compound is an inhibitor of phosphatidylinositol 3-kinase activity. To compare enzyme activity levels, the amount of labeled, phosphorylated substrate can be quantified. Under such in vitro kinase assay conditions, if the enzymatic activity in the presence of a test inhibitory substance is reduced by at least 25% compared to the activity of the control in the absence of the substance, then the enzyme activity is considered "significantly reduced."

A substance is also considered inhibitory of phosphatidylinositol 3-kinase activity if it blocks cellular responses normally observed with the constitutively active kinase. Such responses are observed in p110* -expressing cells independent of growth factor activation and include and the activation of the fos promoter. This in vivo inhibition can be tested in cells transfected with and expressing p110* by exposing the intracellular p110* kinase to test inhibitory substances. The cell can be exposed to or contacted with test substances that are peptides or small molecules by adding the substances in solution into the media and allowing the uptake of these substances into the cell. A test substance can also be introduced into the cell by other methods, e.g., by microinjection or transfection of a DNA encoding the substance. p110*-expressing cells in the presence and absence of the test inhibitory substances are analyzed for cellular responses normally observed with the constitutively active kinase independent of growth factor stimulation. Such responses include induction of gene expression by fos-promoter activation, pp70 S6-kinase activation, membrane ruffling (in mammalian cells), *Xenopus laevis* oocyte maturation, activation of ras, raf, MAP-kinase (in *Xenopus laevis* oocytes). For example, NIH 3T3 can be co-transfected with a vector p110* and a pfos-luc construct as described in the experimental examples. Transcription from the fos promoter can be detected by assaying for luciferase activity.

The test substance or compound can be naturally occurring or synthetic and includes drugs, proteins, peptides, lipids, sugars and recombinantly produced substances.

The constitutively active kinase or antagonists of the kinase activity are useful in therapeutic formulations for the treatment of various disease conditions as described above. A formulation comprising an inhibitor of phosphatidylinositol 3-kinase activity in an amount therapeutically effective to block phosphatidylinositol 3-kinase activity in affected cells of the patient, can be administered to the patient. The affected cells can be tumor cells or other proliferative cells. Therapeutic formulations of the constitutively active phosphatidylinositol 3-kinase polypeptide or formulations of the inhibitors of the kinase can be prepared and administered as follows.

The formulations can be administered locally or systemically in pharmaceutically acceptable carriers such as saline, phosphate buffered saline, or a controlled release formulation. The dosage level and mode of administration of the protein composition depend on the nature of the protein, the nature of the condition to be treated, and the history of the individual patient. Systemic administration is generally required, which may be by injection or by transmucosal or transdermal delivery. Administration by injection may be intravenous, intramuscular, intraperitoneal or subcutaneous. Formulations for injection are generally biocompatible solutions of the active ingredient such as Hank's solution or Ringer's solution. Formulations for transdermal or transmucosal administration generally include penetrants such as fusidic acid or bile salts in combination with detergents or surface-active agents. The formulations can then be manufactured as suppositories or patches. Oral administration is generally not favored for protein or peptide active ingredients; however, if suitably formulated so as to be protected from the digestive enzymes, oral administration can also be employed.

Drug delivery vehicles such as liposomes, can be used to deliver and provide sustained release of the formulations in the body. The liposomes can have targeting moieties exposed on the surface such as antibodies, ligands or receptors to specific cell surface molecules. For example, it may be desirable to limit the delivery of the formulation to only tumor cells. Such cells can be targeted to receive the therapeutic formulation by incorporating into the liposome carrier, a targeting moiety that recognizes and binds a specific tumor surface marker. Liposome drug delivery is known in the art (see, e.g., Biochimica et Biophysica Acta, 113:201–227 (1992)).

Suitable formulations for a desired mode of administration can be found in Remington's Pharmaceutical Sciences, latest edition, Mack Publishing Co., Easton, Pa. The dosage levels and precise formulations are obtainable by routine optimization procedures as is generally known in the art.

A therapeutic formulation for use in vivo generally will contain a "pharmaceutically acceptable carrier". By this is intended either solid or liquid material, which may be inorganic or organic and of synthetic or natural origin, with which the active component of the composition is mixed or formulated to facilitate administration to a subject. Any other materials customarily employed in formulating pharmaceutical are suitable. Solid carriers include natural and synthetic cloisonne silicates, for example natural silicates such as diatomaceous earths; magnesium silicates, for example talcs; magnesium aluminum silicates, for example attapulgites and vermiculites; aluminum silicates, for example kaolinites, montmorillonites, and micas; calcium carbonate; calcium sulfate; synthetic hydrated silicone oxides and synthetic calcium or aluminum silicates; elements such as carbon or sulfur; natural and synthetic resins such as polyvinyl alcohol; and waxes such as paraffin and beeswax. Examples of suitable liquid carriers include water and aqueous solutions containing oxygenated organic compounds such as ethanol. Buffers and other materials normally present in pharmaceutical preparations, such as flavoring and suspending agents, can also be present. Pharmaceutical carriers differ from typical solutions and suspensions in that they are specifically prepared for use in vivo to exclude substances that may be harmful to the patient to whom the formulation is administered.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Experimental Examples

The following examples are by way of illustration and are not to be construed as a limitation on the scope of the invention.

EXAMPLE 1

Construction of p110*

To generate an activated p110 mutant, p110*, the iSH2 region of p85 was covalently attached to the N-terminus of p110. A hinge region composed of a "glycine-kinker" was inserted between iSH2 and p110 to allow the iSH2 domain to more easily interact with the p110 N-terminal domain (FIG. 1). P110 constructs were tagged at the C-terminus with the myc epitope (oval); the iSH2 fragment of p85 contained a C-terminal influenza virus hemagglutinin (HA) epitope tag (diamond) (FIG. 1).

Vectors directing the expression of HA-tagged p85, iSH2 or myc-tagged p110 have been described (Klippel et al., Mol. Cell. Biol., 13:5560 (1993); Klippel et al., Mol. Cell. Biol., 14:2685 (1994)). The GenBank accession number for the mouse p85 cDNA sequence is M60651. The coding region for the 102-amino-acid iSH2 fragment of p85 was generated by PCR with mouse p85α cDNA (Escobedo et al., Cell, 65:75–82 (1991)) as the template with primer iSHV-s-(5'<u>CTT CTA GAA TGG CTC ATA TGT</u> TAT ATG AGG AGT ACA CCC GT 3' SEQ. ID. NO. 3), containing nucleotides 1396 to 1416 of the coding strand extended BY XbaI and NdeI restriction sites, and primer iSHV-α(5' <u>T CCC GGG</u> CTT AAT ACT GTT CAT GCG 3' SEQ. ID. NO. 4) containing nucleotides 1684 to 2001 of the noncoding strand extended by a SmaI-XmaI restriction site (A of the start codon is designated nucleotide 1, and nucleotides that are changed with respect to the wild-type sequence are underlined). The sequence was confirmed by DNA sequence analysis. For expression in mammalian cells, the iSH2 DNA fragment was ligated via XbaI-XmaI ends into a modified version of vector pCG carrying the 16-amino-acid HA epitope tag (Klippel et al., Mol. Cell. Biol., 13:5560–5566 (1993)) (SYPYDVPDYASLGGPS; SEQ ID NO:13 [Wilson et al., Cell, 37:767–778 (1984)]). pCG which is a derivative of pEVRF (Matthias et al., Nucleic Acids Res., 17:6418 (1989)) with a modified polylinker, directs expression in mammalian cells from the human cytomegalovirus promoter/enhancer region; translation initiation is controlled by the 5' untranslated region of the herpes simplex virus thymidine kinase gene. pCG carrying the HA epitope was constructed as follows. A tagged C-terminal SH2 domain of p85 was generated by using p85α cDNA as the template with primer tk.SH2-C (5' <u>CT TCT AGA ATG GCT CAT ATG</u> AAA CGC GAA GGC AAC GAG AAA GAA 3' SEQ NO. 5), containing nucleotides 1537 to 1560 of the coding strand extended by XbaI and NdeI restriction sites, and primer SH2-C.HA (5' <u>TAT GGA TCC TCA GGA AGG TCC TCC CAG GCT GGC ATA GTC AGG CAC GTC ATA AGG ATA GCT TCC CCC GGG</u> TCG CCT CTG TTG TGC ATA TAC TGG GTA 3' SEQ NO. 6). This generated fragments in which the wild-type p85 coding region was extended by sequences encoding amino acids PGG as a hinge region (overlapping a SmaI site), which precedes the 16-amino acid HA epitope, followed by a stop codon and a BamHI site. The DNA ends were repaired with T4 DNA polymerase and phosphorylated with T4 polynucleotide kinase.

The GenBank accession number for the mouse p110 cDNA sequence is U03279. The mouse p110 CDNA was cloned into the polylinker of vector pKS(+) at EcoRI (5') and NotI (3') sites. To modify the C-terminal end of p110 with the 10-amino-acid Myc epitope (EQKLISEEDL; SEQ ID NO:1 [Evan et al., *Mol. Cell. Biol.*, 5:3610–3616 (1985)]), a C-terminal fragment of the cDNA was amplified with primer p110-3' HindIII (5' CTG AGC AAG AAG CTT TGG 3' SEQ NO. 10), consisting of nucleotides 3092 to 3109 of the coding strand overlapping a HindIII site, and primer p110.-Myc (5' GGA TCC TCA GTT CAG GTC CTC CTC GGA AAT CAG CTT CTG CTC CCC GAG CTC GTT CAA AGC ATG CTG CTT GAT GGT GTG G 3' SEQ NO. 7) containing nucleotides 3177 to 3204 of the noncoding strand (A of the start codon is designated nucleotide 1, and nucleotides that are changed with respect to the wild-type sequence are underlined). This extended the p110 C-terminal end by a sequence encoding amino acids DLG as a hinge region (overlapping a SacI-Ecl13611 site), which precedes the coding region for the Myc epitope, a stop codon, and a BamHI restriction site. The wild-type C-terminal end was exchanged for the Myc-tagged sequence with HindIII and BamHI. The N-terminal end of the p110 coding region was modified by PCR with primer p110-5'BsmI (5' GGC CTG AGG AGG CAT TCT AAA G 3' SEQ. ID NO. 8), consisting of nucleotides 98 to 120 of the noncoding strand overlapping a BsmI site, and primer p110–350 (5' TCT AGA ATG GCT CAT ATG CCT CCA CGA CCA TCT TCG 3' SEQ NO. 9) containing nucleotides 1 to 21 of the coding strand extended by XbaI and NdeI restriction sites. The wild-type N terminus was replaced by the newly generated N-terminal end via XbaI-BsmI sites. The correct sequence of the p110 fragments modified by PCR was confirmed by DNA sequence analysis. p110Δ61, which lacks the N-terminal 61 amino acids of full-length p110, was constructed by fusing the p110 coding region, after blunting the AlwNI site at nucleotide 187, to an ATG of the modified p110 N-terminal region described above. p110Δ123 lacking the first 123 amino acids was generated in parallel by fusion of the blunted SphI site at nucleotide 370 in frame to a start codon. For expression of full-length p110 and truncated p110 molecules tagged with the Myc epitope in COS-7 cells, the respective DNA fragments were cloned into mammalian expression vector pCG (see above) via XbaI-BamHI ends.

HA-tagged molecules were recognized by murine anti-influenza virus hemagglutinin monoclonal antibody 12CA5 (Wilson et al., *Cell*, 37:767 (1984)); myc-tagged p110 derivatives were detected using murine anti-myc monoclonal antibody 9E10 (Evan et al., *Mol. Cell. Biol.*, 5:3610 (1985)). pCG-p110 Δkin.myc was obtained from pCG-p110.myc (Klippel et al., *Mol. Cell. Biol.*, 14:2685 (1994)) by deleting nucleotides coding for the ATP-binding motif within the p110 kinase domain using restriction endonucleases Bsr FI and Mae II. The expressed protein lacks amino acids 917 to 950 of wt p110. Expression vectors encoding chimeric p110*, p110* Δ61 and p110*Δ123 molecules (FIG. 1) were derived from previously described precursors (Klippel et al., *Mol. Cell. Biol.*, 14:2685 (1994)). A fragment encoding the p85 iSH2 domain (Klippel et al., *Mol. Cell. Biol.*, 14:2685 (1994)) was fused in frame at its C-terminus to the "glycine kinker" region in vector pGEX-KG (Guan et al., *Analyt. Biochemistry*, 192:262 (1991)). The iSH2 -glycine kinker fragment was then ligated via Xba I ends to the N-terminus of p110 derivatives. p110* chimera with internal deletions were generated using pCG-p110.myc and reconstituted with the iSH2-glycine kinker fragment described above; p110* ΔI lacks the Bst BI fragment of the mouse p110 coding region; in p110* ΔII an Asp 700-Afl II fragment was deleted; p110* ΔIII is deleted for a large portion of the presumed p110 kinase region (between Hpa I and Hind III). The corresponding amino acid deletions in these mutant proteins are depicted in FIG. 1.

In FIG. 1, the p110 region with homology to the catalytic domain of protein kinases (Hiles et al., *Cell*, 70:419 (1992)) is depicted by a box labelled "kinase." The domain responsible for the interactions with the iSH2 domain of the p85 subunit is shown as a smaller box at the p110 N-terminus. P110Δkin is a kinase-deficient p110 in which the ATP-binding site was mutated as described above and indicated by an asterisk within the catalytic domain. The iSH2 domain of p85 that is required for catalytic activity is represented by a hatched bar. The first and last amino acids of fragments are numbered with respect to their position of the wt p85 or p110 sequence. FIG. 1 shows a panel of p85–p110 chimeric proteins. P110* is a constitutively active chimera that contains the iSH2 domain of p85 fused to the N-terminus of p110 via a flexible "glycine-kinker." P110*Δkin is the kinase deficient version of p110*. P110*Δ61 and p110*Δ123 lack the first 61 or 123 amino acids counting from the p110 N-terminus respectively and can no longer associate with iSH2. P110*ΔI, p110*ΔII and p110*ΔIII are mutants that have internal deletions within the p110 structure as indicated.

EXAMPLE 2

Kinase activities of p110* and derivatives

Figure 2A:
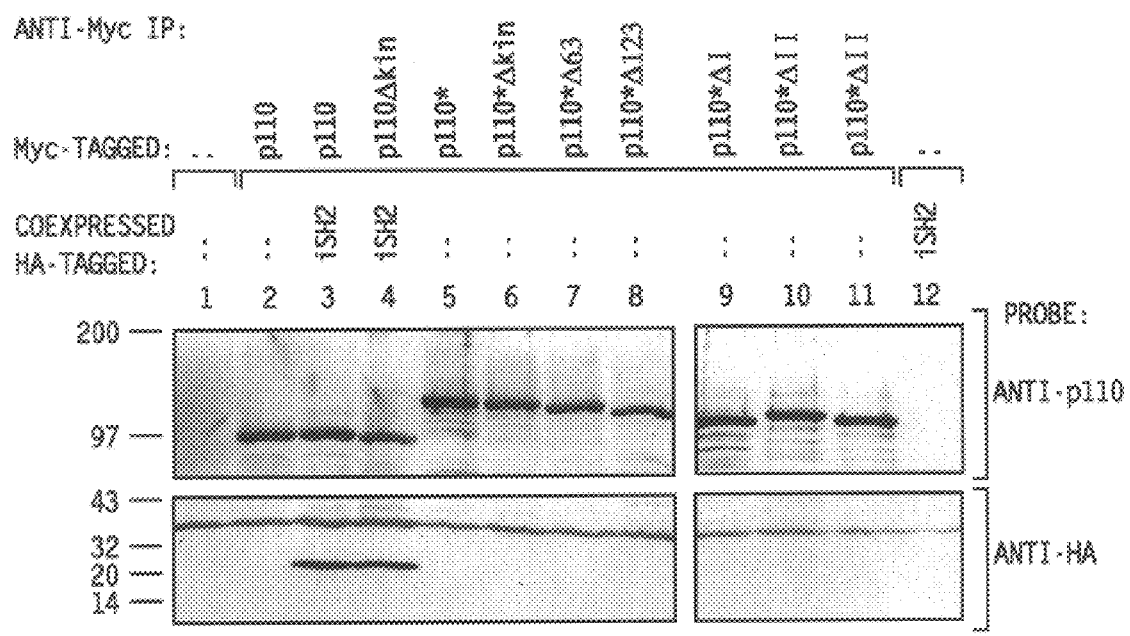
FIGS. 2A, 2B and 2C show the results of the functional characterization of the constitutively active p110* and its derivatives.

The activated p110 mutant (p110*) and its derivatives, shown in FIG. 1 were characterized with respect to phosphatidylinositol 3-kinase activity and protein kinase activity. All p110 derivatives were transfected into COS 7 cells using DEAE-Dextran, transiently expressed and lysed as described in detail in (Klippel et al., *Mol. Cell. Biol.*, 14:2685 (1994)). Wt p110 and its kinase defective version, p110 Δkin, served as controls in both phosphatidylinositol-3 and protein kinase assays and were expressed alone (—) or coexpressed with the iSH2 fragment of p85 as indicated in FIG. 2. myc-tagged p110 or p110* molecules were immunoprecipitated (IP) from cell lysates using anti-myc antibody 9E10 as described previously (Klippel et al., *Mol. Cell. Biol.*, 14:2675–2685 (1994)). p110 molecules or the HA-tagged iSH2 fragment were detected by immunoblotting (FIG. 2A) with anti-p110 or anti-HA antibodies, respectively. Half of the extensively washed immunocomplexes were subjected to an in vitro-kinase reaction [in 50 μl 30 mM Tris-HCl, pH 7.5, 10 mM MnCl$_2$, 10 μCi [γ$^{-32}$P]ATP for 20 min at 25° C.], separated by SDS-PAGE (7 to 12%) and transferred to nitrocellulose. The second half of the immunocomplexes was analyzed for phosphatidylinositol 3-kinase activity. The production of radiolabeled phosphatidylinositol 3-phosphate (PIP), as evidence of phosphatidylinositol 3-kinase activity, was analyzed by thin-layer chromatography (Kaplan et al., *Cell*, 50:1021 (1987); Whitman et al., *Nature*, 332:644 (1988)).

Figure 2B:
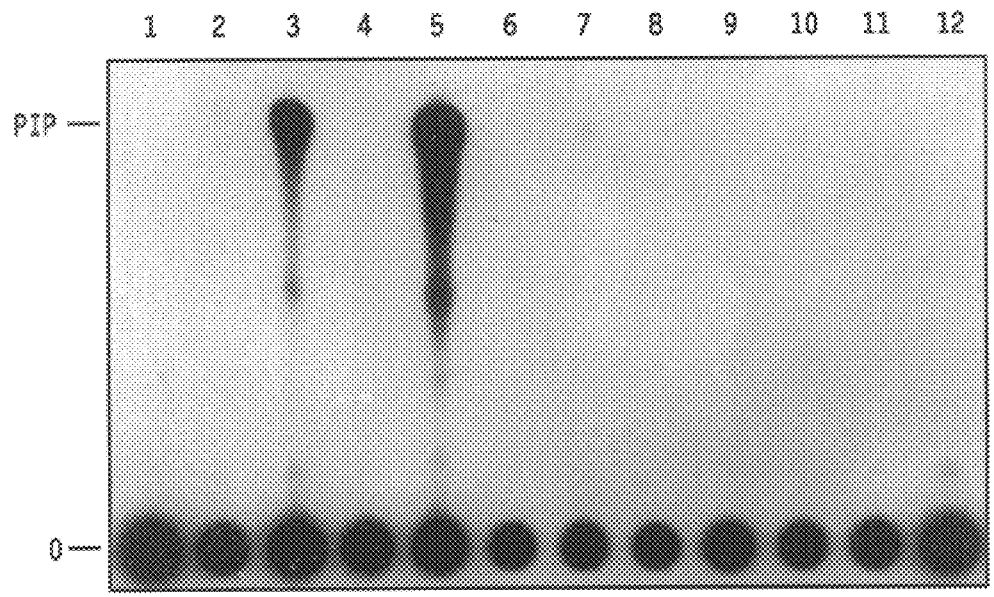

The results of the phosphatidylinositol 3-kinase assay are shown in FIG. 2B. Note that in FIGS. 2B and C, the numbers above the lanes correspond to those of the samples shown in FIG. 2A. The origin (O) of the chromatogram and the position of PIP are indicated. p110* (lane 5) had reproducibly higher specific phosphatidylinositol 3-kinase activity than wt p110 coexpressed with iSH2 (lane 3). This may be due to the fact that in p110*, an intramolecular interaction between iSH2 and p110 is kinetically favored. The level of p110 or p110* expression was very similar in all the samples as can be seen by the intensity of the bands detected by immunoblotting in FIG. 2A.

Figure 2C:
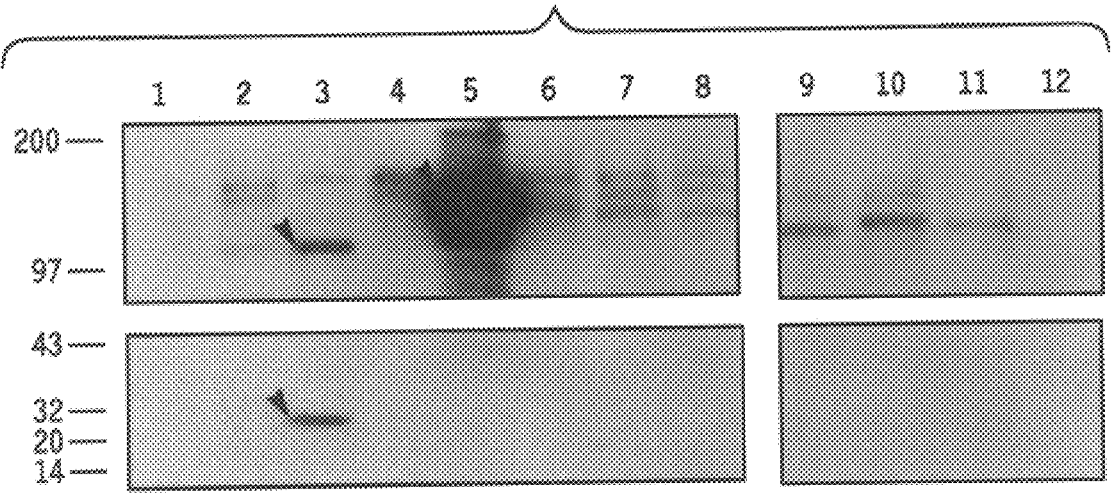

P110 also possessed protein kinase activity as evidenced by the detection of phosphoproteins in the anti-myc immunoprecipitates (FIG. 2C). In FIG. 2C, the positions of phosphorylated p110, iSH2 and p110* are indicated by arrowheads. Weaker signals are due to an unspecific protein kinase present in the immunoprecipitates. As with phosphatidylinositol 3-kinase activity, the protein kinase activity of p110, measured in an autophosphorylation assay, was dependent upon its association with iSH2 (FIG. 2C). Kinase-deficient versions of p110 which were mutated within the putative ATP-binding site exhibited neither phosphatidylinositol 3-kinase nor protein kinase activity above background level. p110*Δ123, in which iSH2 was fused to a truncated N-terminus of p110, had neither phosphatidylinositol 3-kinase nor protein kinase activity (FIG. 2B, C). This finding indicates that the mere presence of iSH2 in cis cannot substitute for the p110 N-terminal region. This implies that the N-terminus of p110 does not simply function to tether iSH2 to the remainder of p110, but also has an intrinsic function in regulating catalytic activity.

EXAMPLE 3

The role of phosphatidylinositol 3-kinase in signaling in vivo

To investigate the role of phosphatidylinositol 3-kinase in growth factor-mediated mitogenic signaling in vivo, p110* was coexpressed in NIH 3T3 cells with a reporter vector in which the expression of luciferase is under the control of the fos promoter (pfos-luc), since the induction of fos expression is one of the earliest responses after growth factor treatment (Wagner et al., *EMBO J.*, 9:4477 (1990)).

Plasmid pfos-luc, in which expression of luciferase is under control of the c-fos promoter was obtained by replacing the coding region for cat of pFC700 (Fish et al., *Mol. Cell. Biol.*, 7:3490 (1987)) with the DNA fragment encoding luciferase from pGL2 (Promega). pBJ-c-ras was constructed by digestion of pV-IKS-c-ras [kindly provided by Kikuchi] with Eco RI and Bgl II. The ras insert was then ligated into vector pBJ downstream of the SRα promoter (Takebe et al., *Mol. Cell. Biol.*, 8:466 (1988)). The DN-ras fragment was isolated from pBSK-DN-ras [kindly provided by A. Kikuchi] after Xho I and Not I digestion and ligated into pBJ DNA. The NAF encoding DNA fragment (MacNicol et al., *Cell*, 73:571 (1993)) was cloned into vector pCG (Klippel et al., *Mol. Cell. Biol.*, 14:2685 (1994)).

NIH 3T3 cells were cotransfected with reporter plasmid pfos-luc and vectors expressing p110*, c-ras, DN-ras or NAF. Transient transfection of NIH 3T3 cells with the indicated expression vectors was carried out by using Lipofectamin (Gibco BRL) according to the manufacturer's instruction. Cells were lysed 48 h after transfection after incubation in serum-free medium in 100 μl of lysis buffer (Promega). Luciferase activity was assayed from one half of the cell lysates. Luciferase activity assays were performed by adding luciferin (from Molecular Probes) using a Luminometer.

Figure 3A:
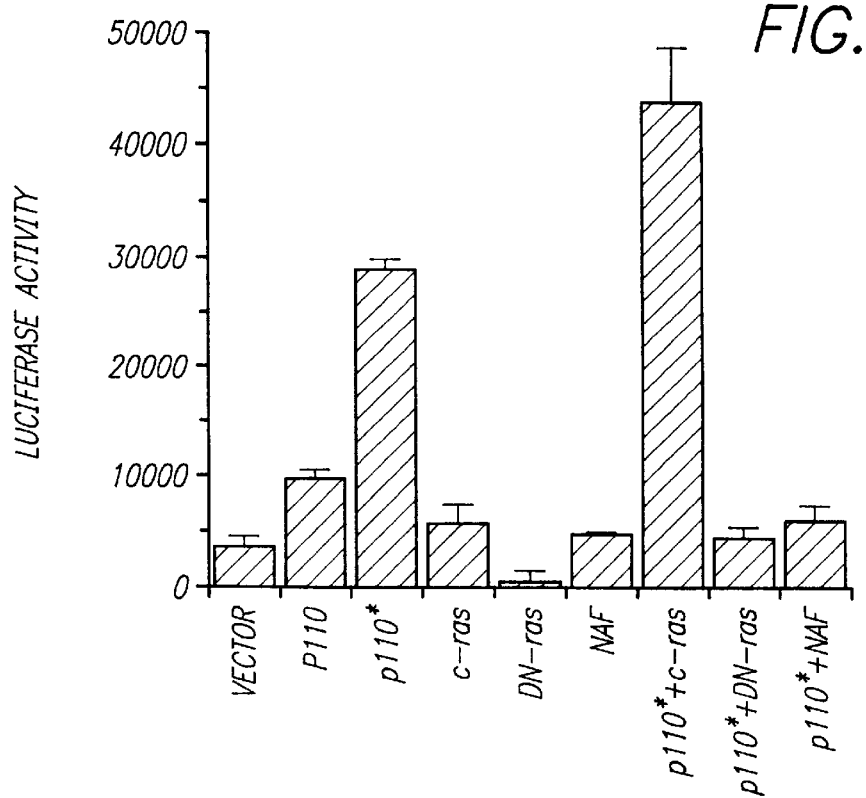
FIGS. 3A and 3B show activation of c-fos promoter by p110* in luciferase assays.
Figure 3B:
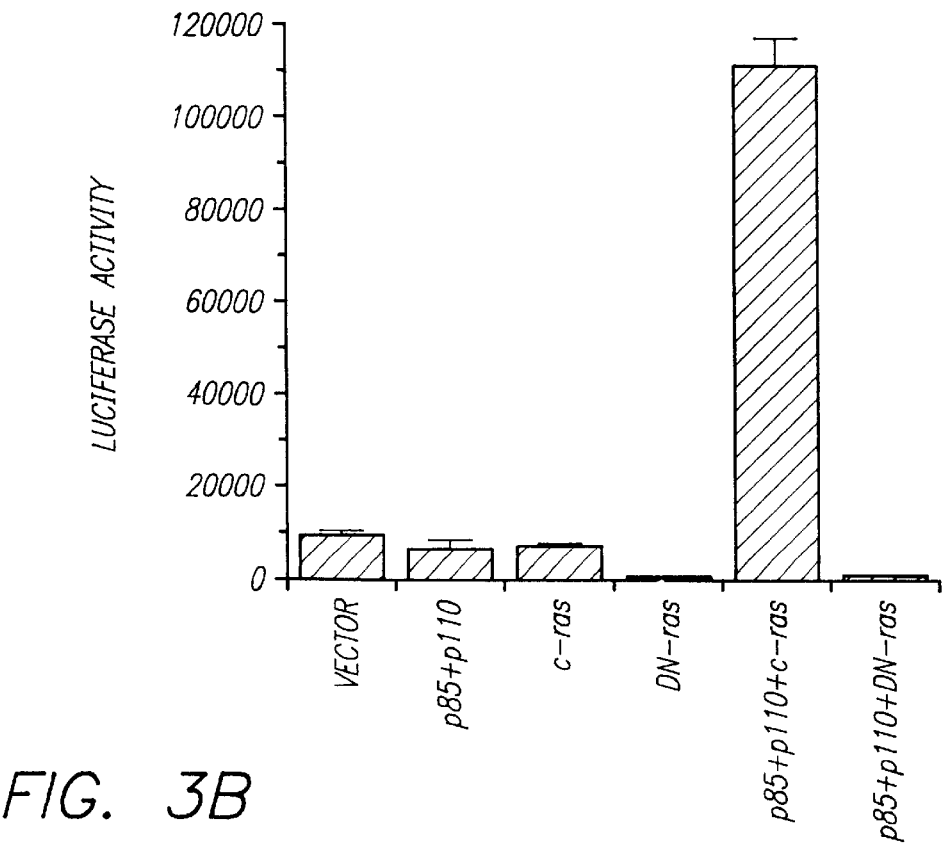

The results of the luciferase assay are shown in FIGS. 3A and 3B. Each bar represents the mean of triplicate samples ± standard deviation. Expression of p110* in the presence of pfos-luc resulted in an increase in luciferase activity as compared to control reactions (FIG. 3A). This activity was potentiated by coexpression of c-ras. In contrast, the activation of the fos promoter by p110* was completely inhibited by coexpression of dominant negative (DN) ras, indicating that p110*-mediated increase in fos promoter activity is dependent upon the ras pathway.

To extend these studies, the effect of dominant negative raf-1(NAF) on p110*-mediated fos promoter activation was tested. Activated ras results in the activation of raf-1. Wild-type raf is a serine kinase which when activated, induces a cascade of phosphorylation events starting with the phosphorylation of MAP kinase and MAP kinase which in turn phosphorylates, and thus, activate transcription factors Elk-1/SAP-1 culminating in the transcription of early response genes such as c-fos and c-myc that are involved in DNA replication and cell division. NAF is an inhibitor of endogenous raf activity (MacNicol et al., *Cell*, 73:571 (1993)). NAF blocked p110* induced activation of the fos promoter (FIG. 3A, lane 9), consistent with the action of raf-1 as an immediate downstream effector of ras. P110* expression levels were not affected by coexpression of c-ras, DN-ras or NAF.

myc-tagged p110* was immunoprecipitated using the second half of the cell lysates assayed in FIG. 3A with anti-myc antibody 9E10, described above. P110* molecules were detected by Western-blotting by using anti-plio antibodies. Murine monoclonal anti-p110 antibodies E2A, HIA and IIA were used as a mixture. They were raised against a purified fragment of mouse p110 (amino acids 575 to 1068) expressed in *E. coli*. The epitope of all three monoclonals was mapped to be outside of the ATP-binding site in the p110 kinase domain. Therefore these antibodies recognize wt p110 and p110 Δkin derivatives equally well.

To test the effect of wt phosphatidylinositol 3-kinase on the fos promoter, expression vectors encoding p85 and p110* were cotransfected with pfos-luc into NIH 3T3 cells (FIG. 3B). The cells were lysed after 48 h and the luciferase activities were assayed as in FIG. 3A. In contrast to the constitutively active phosphatidylinositol 3-kinase, p110*, the wt p85/p110 complex did not activate the fos promoter to significant extent unless it was coexpressed with c-ras (FIG. 3B). This suggests that p85 not only has a stimulatory effect on the enzymatic activities of p110, mediated by its iSH2 region, but that it might also have negative regulatory function (Carpenter et al., *Mol. Cell. Biol.*, 13:1657 (1993); Dhand et al., *EMBO J.*, 13:522 (1994)). For example, the additional domains present in p85 could prohibit the wt phosphatidylinositol 3-kinase complex from acting in a constitutively active fashion.

Figure 5B:
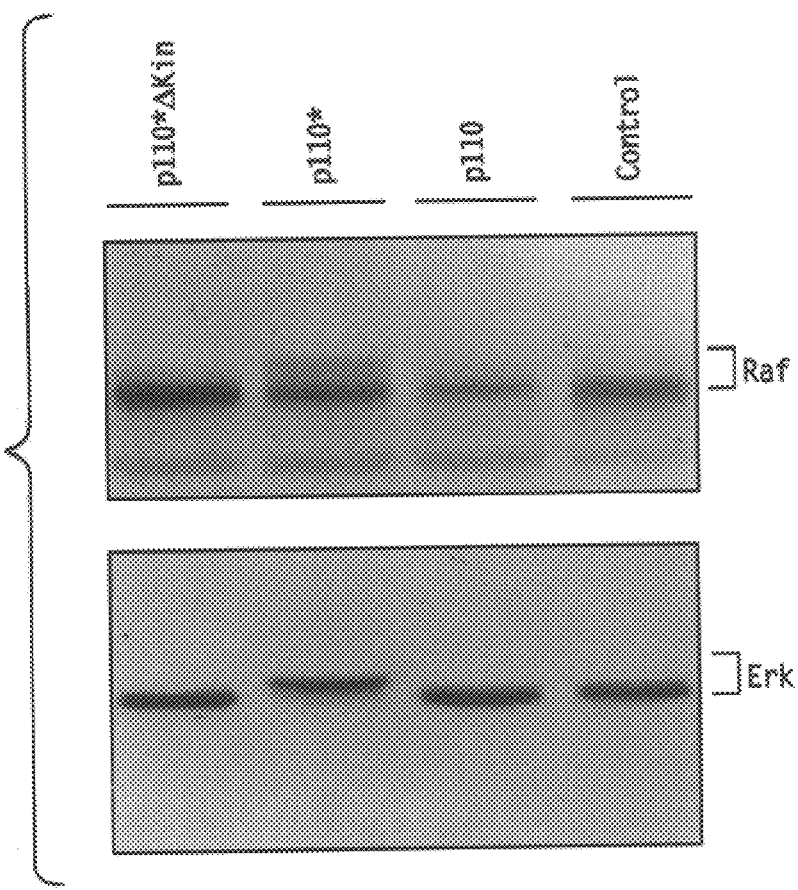
FIGS. 5A, 5B and 5C show that the phosphatidylinositol 3-kinase expression in *Xenopus laevis* oocytes leads to activation of the ras-signaling pathway. PDGF-R stands for PDGF receptor.
Figure 5A:
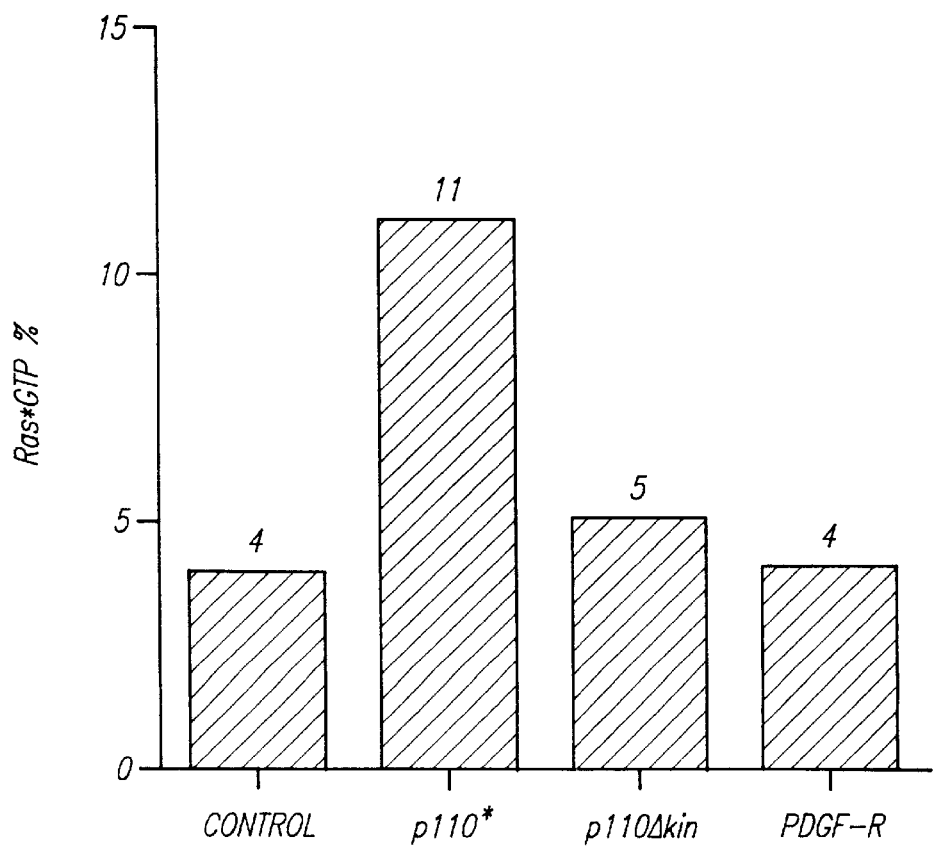
Figure 5C:
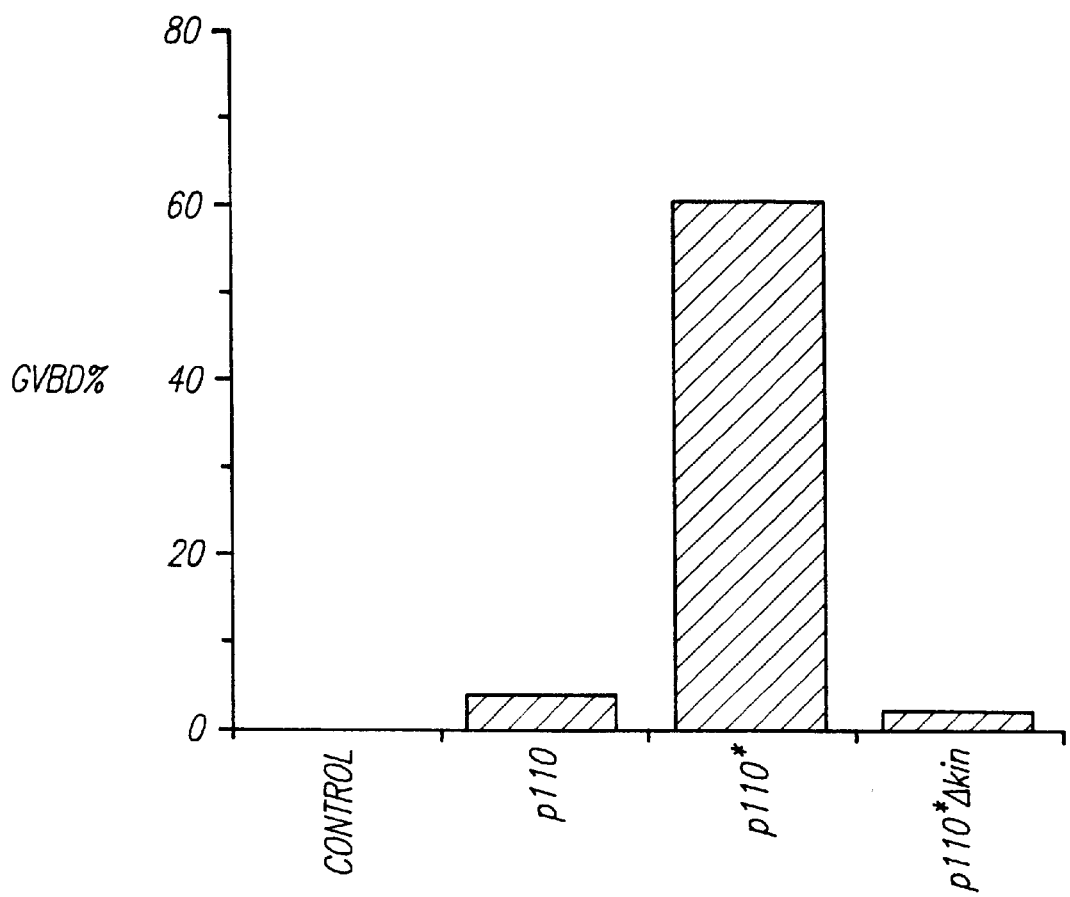

To investigate in another system, whether phosphatidylinositol 3-kinase can activate the ras pathway, myc-tagged p110* was transiently expressed in *Xenopus laevis* oocytes by RNA injection. Oocytes were isolated and injected with the indicated RNAs as described (Muslin et al., *Mol. Cell. Biol.*, 13:4197 (1993)). The results are shown in FIGS. 5A–C. The expression levels of the p110 derivatives were comparable in all samples (not shown). Each panel shows results of a representative experiment. Each experiment was performed at least twice. At least 45 oocytes were injected per condition. FIG. 5A shows ras.GTP levels determined as described (Satoh et al., *Proc. Natl. Acad. Sci. USA*, 87:5993 (1990)). The oocytes were labeled 24 hours using 0.5 mCi of $^{32}$P-orthophosphate per sample. The ratio of ras.GTP/(ras.GDP+ras.GTP) was determined. In FIG. 5B, the activation state of downstream effectors of ras oocyte lysates were separated by SDS-PAGE and analyzed by immunoblotting with antibodies to raf or erk (Muslin et al., *Mol. Cell. Biol.*, 13:4197 (1993)). In FIG. 5C, oocyte maturation was scored 24 hours postinjection and is shown as % germinal vesical breakdown (GVBD).

In oocytes expressing p110*, the level of GTP-bound ras (ras.GTP) was increased more than twofold compared to controls (FIG. 5A). ras activation was accompanied by activation of the downstream effectors raf-1and Erk as indicated by retarded gel-electrophoretic mobility (FIG. 5B). Consistent with the known ability of activated forms of ras to induce maturation (Trahey et al., *Science*, 238:542 (1987)) oocytes expressing p110* matured, whereas oocytes expressing a "kinase-negative" mutant of p110 did not (FIG. 5C). This correlated with the finding that only lysates of oocytes injected with p110* RNA had phosphatidylinositol 3-kinase activity that could be precipitated by an antibody recognizing the myc-tag (not shown). Coexpression of DN-ras decreased the degree of p110* induced oocyte maturation. This set of experiments showed that expression of p110* leads to an increase in ras-GTP in Xenopus oocytes, which mediates activation of raf and erk and maturation of the oocytes. These results indicate that phosphatidylinositol 3-kinase can act upstream of ras in this system.

EXAMPLE 4
Region of p110 important for activation of fos promoter

Figure 4:
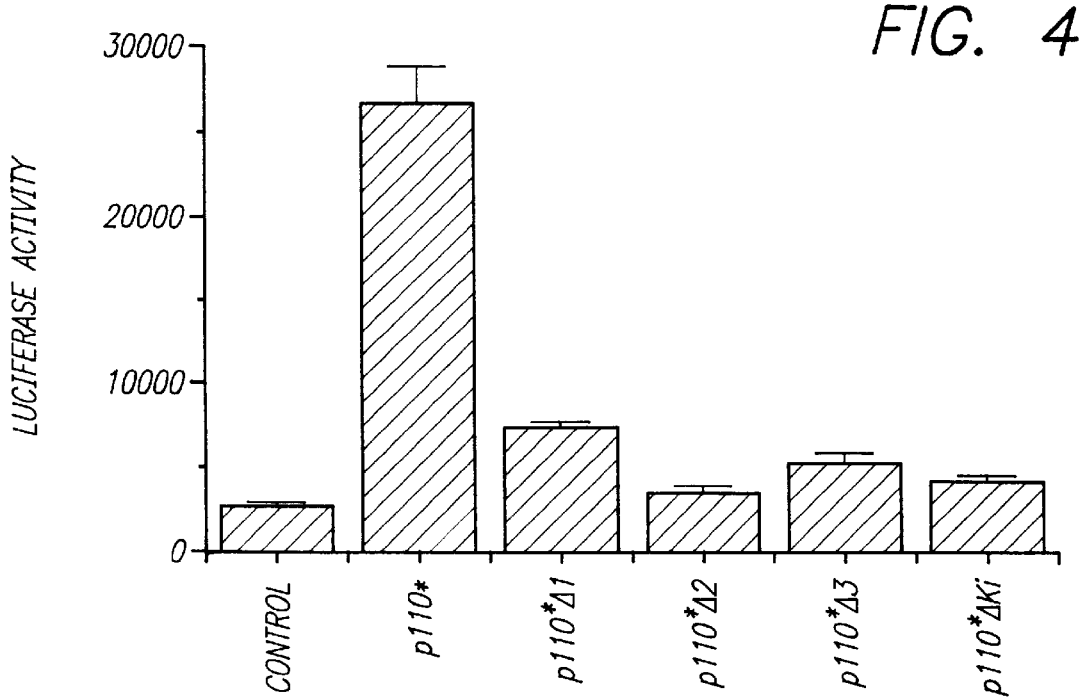
FIG. 4 shows the effect of various truncation mutants of p110* (FIG. 1) on the fos promoter by luciferase assay (p110*Δ1, Δ2, Δ3, Δki correspond to p110*ΔI, ΔII, ΔIII and Δkin, respectively, shown in FIG. 1).

To determine which part of p110 was important for activation of the fos promoter, several deletion mutants of p110 were tested in the luciferase assay (FIG. 4). P110* mutants that were inactive in both phosphatidylinositol 3-kinase and protein kinase activities (see FIGS. 2B, C) were also severely impaired in activating the fos promoter, indicating that kinase activities of p110 were necessary for fos induction.

It has been shown that yeast strains defective in phosphatidylinositol 3-kinase do not grow normally (Herman et al., *Trends Cell Biol.*, 2:363 (1992); Schu et al., *Science*, 260:88 (1993); Stack et al., *EMBO J.*, 12:2195 (1993)). Previous studies have used mutant receptors or phosphatidylinositol 3-kinase inhibitors to examine phosphatidylinositol 3-kinase function. For example, mammalian cells transfected with receptor molecules unable to bind phosphatidylinositol 3-kinase were defective in growth factor stimulated mitogenesis, receptor internalization and cell migration (Fantl et al., *Cell*, 69:413 (1992); Valius et al., ibid., 73:321 (1993); Joly et al., *Science*, 264:684 (1994); Kundra et al., *Nature*, 367:474 (1994)).

The results herein show for the first time that phosphatidylinositol 3-kinase can activate two pathways, one that is important in the mitogenic response to most growth factors in mammalian cells, and the other for Xenopus oocyte maturation. The stimulation of fos promoter activity by phosphatidylinositol 3-kinase requires the ras/raf pathway. An elevated level of GTP-bound ras in response to p110* expression in oocytes was direct evidence that phosphatidylinositol 3-kinase can activate the ras pathway.

All the information contained in the references and patent documents cited above is incorporated herein by reference.

What is claimed is:

1. A constitutively active phosphatidylinositol 3-kinase polypeptide comprising a p85 subunit iSH2 domain sequence or a conservatively modified variant thereof linked at the carboxy-terminus by a linker to the amino-terminus of a p110 subunit or a conservatively modified variant thereof.

2. The polypeptide of claim 1, wherein the N-terminal 20 amino acids are eliminated from the p110 subunit.

3. The polypeptide of claim 1, wherein the iSH2 domain sequence is selected from the group of sequences consisting of amino acids 466 to 567 of the p85 of SEQ. ID NO 11 subunit, amino acids 434 to 599 of the p85 of SEQ ID NO: 11 subunit, and conservatively modified variants thereof.

4. The polypeptide of claim 1 further comprising a tag at the amino or carboxy terminus.

5. The polypeptide of claim 4, wherein the tag is an epitope.

6. The polypeptide of claim 5, wherein the epitope tag is a myc epitope at the carboxy terminus of the p110 subunit.

7. A constitutively active phosphatidylinositol 3-kinase polypeptide, comprising amino acids 466 to 567 of the p85 of SEQ ID NO: 11 subunit iSH2 domain linked by a 10 amino acid glycine kinker to a p110 subunit at the amino-terminus of the p110 subunit, and a myc epitope as defined by SEQ ID NO. 1 (EQKLISEEDL) fused to the carboxy terminus of the p110 subunit.

8. A method of producing an inositol phosphate product comprising reacting a phosphatidylinositol 3-kinase polypeptide of claim 1 or 7 with a phosphoinositide lipid substrate under appropriate kinase reaction conditions, and isolating the resultant product.

9. The method of claim 8, wherein the product is phosphatidylinositol 3'-phosphate (PI 3'-P) and the lipid substrate is phosphatidylinositol (PI).

10. The method of claim 8, wherein the product is phosphatidylinositol 3',4'-bisphosphate (PI 3',4'-$P_2$) and the lipid substrate is phosphatidylinositol 4'-phosphate (PI 4'-P).

11. The method of claim 8, wherein the product is phosphatidylinositol 3', 4',5'-phosphate (PI 3',4',5'-$P_3$) and the lipid substrate is phosphatidylinositol 4',5'-bisphosphate (PI 4',5'-$P_2$).

12. A kit for preparing an inositol phosphate product, comprising:
    a constitutively active phosphatidylinositol 3-kinase polypeptide of claim 1 or 7; one or more phosphoinositide substrates; and instructions for preparing the inositol phosphate reagent.

13. The kit of claim 12, further comprising a buffer for reconstituting said phosphatidylinositol 3-kinase polypeptide and a reaction buffer.

14. The kit of claim 12, wherein the inositol phosphate product is selected from the group consisting of PI 3-P, PI 3',4'-$P_2$, and PI 3',4',5'-$P_3$.

15. The kit of claim 12, wherein the phosphoinositide substrate is selected from the group consisting of PI, PI 4'-P, and PI 4',5'-$P_2$.

* * * * *

```
                         SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Glu Gln Lys Leu Ile Ser Glu Glu Asp Leu
1               5                   10

(2) INFORMATION FOR SEQ ID NO:2:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Gly Gly Ile Ser Gly Gly Gly Gly Ile
1               5                   10

(2) INFORMATION FOR SEQ ID NO:3:

(i) SEQUENCE CHARACTERISTICS:
         (A) LENGTH: 41 base pairs
         (B) TYPE: nucleic acid
         (C) STRANDEDNESS: single
         (D) TOPOLOGY: linear
```

(ii) MOLECULE TYPE: DNA (xi) SEQUENCE DESCRIPTION: SEQ ID NO:3:

CTTCTAGAAT GGCTCATATG TTATATGAGG AGTACACCCG T              41

(2) INFORMATION FOR SEQ ID NO:4:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

TCCCGGGCTT AATACTGTTC ATGCG                                25

(2) INFORMATION FOR SEQ ID NO:5:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

CTTCTAGAAT GGCTCATATG AAACGCGAAG GCAACGAGAA AGAA            44

(2) INFORMATION FOR SEQ ID NO:6:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

TATGGATCCT CAGGAAGGTC CTCCCAGGCT GGCATAGTCA GGCACGTCAT AAGGATAGCT    60

TCCCCCGGGT CGCCTCTGTT GTGCATATAC TGGGTA                             96

(2) INFORMATION FOR SEQ ID NO:7:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

GGATCCTCAG TTCAGGTCCT CCTCGGAAAT CAGCTTCTGC TCCCCGAGCT CGTTCAAAGC    60

ATGCTGCTTG ATGGTGTGG                                                79

(2) INFORMATION FOR SEQ ID NO:8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

GGCCTGAGGA GGCATTCTAA AG                                                    22

(2) INFORMATION FOR SEQ ID NO:9:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

TCTAGAATGG CTCATATGCC TCCACGACCA TCTTCG                                     36

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

CTGAGCAAGA AGCTTTGG                                                         18

(2) INFORMATION FOR SEQ ID NO:11:

(i) SEQUENCE CHARACTERISTICS:
            (A) LENGTH: 1068 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:11:

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
                20                  25                  30

Thr Leu Glu Cys Leu Arg Glu Ala Thr Leu Val Thr Ile Lys His Glu
            35                  40                  45

Leu Phe Arg Glu Ala Arg Lys Tyr Pro Leu His Gln Leu Leu Gln Asp
        50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
                100                 105                 110

Leu Asn Arg Glu Ile Gly Phe Val Ile Gly Met Pro Val Cys Glu Phe
            115                 120                 125

Asp Met Val Lys Asp Pro Glu Val Gln Asp Phe Arg Arg Asn Ile Leu
        130                 135                 140

Asn Val Cys Lys Glu Ala Val Asp Leu Arg Asp Leu Asn Ser Pro His
145                 150                 155                 160

-continued

```
Ser Arg Ala Met Tyr Val Tyr Pro Pro Asn Val Glu Ser Ser Pro Glu
            165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
            195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
            245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
            275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
            325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Leu Ala
385                 390                 395                 400

Arg Leu Cys Leu Ser Ile Cys Ser Val Lys Gly Arg Lys Gly Ala Lys
            405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
            485                 490                 495

Asn Trp Ser Val Ser Arg Glu Ala Gly Phe Ser Tyr Ser His Thr Gly
            500                 505                 510

Leu Ser Asn Arg Leu Ala Arg Asp Asn Glu Leu Arg Glu Asn Asp Lys
            515                 520                 525

Glu Gln Leu Arg Ala Leu Cys Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
            565                 570                 575
```

-continued

```
Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Ser Phe Ala Val Arg Cys Leu Glu Lys Tyr Leu Thr
            610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                    645                 650                 655

Ala Leu Thr Asn Gln Arg Ile Gly His Phe Phe Trp His Leu Lys
            660                 665                 670

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
            690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                    725                 730                 735

Glu Gln Met Arg Gln Pro Asp Phe Met Asp Ala Leu Gln Gly Phe Leu
            740                 745                 750

Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
            770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                    805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
            850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                    885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
            915                 920                 925

Leu Phe His Ile Asp Phe Gly His Phe Leu Asp His Lys Lys Lys Lys
            930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                    965                 970                 975

Phe Glu Arg Phe Gln Glu Met Cys Tyr Lys Ala Tyr Leu Ala Ile Arg
            980                 985                 990
```

```
Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg Lys
        1010                1015                1020

Thr Leu Ala Leu Asp Lys Thr Glu Gln Glu Ala Leu Glu Tyr Phe Thr
1025                1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn
        1060                1065

(2) INFORMATION FOR SEQ ID NO:12:

(i) SEQUENCE CHARACTERISTICS:
        (A) LENGTH: 722 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
                20                  25                  30

Asn Lys Gly Ser Leu Val Ala Leu Gly Phe Ser Asp Gly Pro Glu Ala
            35                  40                  45

Arg Pro Glu Asp Ile Gly Trp Leu Asn Gly Tyr Asn Glu Thr Thr Gly
50                  55                  60

Glu Arg Gly Asp Phe Pro Gly Thr Tyr Val Glu Tyr Ile Gly Arg Lys
65                  70                  75                  80

Arg Ile Ser Pro Pro Thr Pro Lys Pro Arg Pro Pro Arg Pro Leu Pro
                85                  90                  95

Val Ala Pro Gly Ser Ser Lys Thr Glu Ala Asp Thr Glu Gln Gln Ala
            100                 105                 110

Leu Pro Leu Pro Asp Leu Ala Glu Gln Phe Ala Pro Pro Asp Val Ala
        115                 120                 125

Pro Pro Leu Leu Ile Lys Leu Leu Glu Ala Ile Glu Lys Lys Gly Leu
130                 135                 140

Glu Cys Ser Thr Leu Tyr Arg Thr Gln Ser Ser Ser Asn Pro Ala Glu
145                 150                 155                 160

Leu Arg Gln Leu Leu Asp Cys Asp Ala Ala Ser Val Asp Leu Glu Met
            165                 170                 175

Ile Asp Val His Val Leu Ala Asp Ala Phe Lys Arg Tyr Leu Ala Asp
        180                 185                 190

Leu Pro Asn Pro Val Ile Pro Val Ala Val Tyr Asn Glu Met Met Ser
        195                 200                 205

Leu Ala Gln Glu Leu Gln Ser Pro Glu Asp Cys Ile Gln Leu Leu Lys
        210                 215                 220

Lys Leu Ile Arg Leu Pro Asn Ile Pro His Gln Cys Trp Leu Thr Leu
225                 230                 235                 240

Gln Tyr Leu Leu Lys His Phe Phe Lys Leu Ser Gln Ala Ser Ser Lys
            245                 250                 255

Asn Leu Leu Asn Ala Arg Val Leu Ser Glu Ile Phe Ser Pro Val Leu
            260                 265                 270
```

-continued

```
Phe Arg Phe Pro Ala Ala Ser Ser Asp Asn Thr Glu His Leu Ile Lys
            275                 280                 285

Ala Ile Glu Ile Leu Ile Ser Thr Glu Trp Asn Glu Arg Gln Pro Ala
            290                 295                 300

Pro Ala Leu Pro Pro Lys Pro Pro Lys Pro Thr Thr Val Ala Asn Asn
305                 310                 315                 320

Ser Met Asn Asn Asn Met Ser Leu Gln Asp Ala Glu Trp Tyr Trp Gly
                    325                 330                 335

Asp Ile Ser Arg Glu Val Asn Glu Lys Leu Arg Asp Thr Ala Asp Gly
                340                 345                 350

Thr Phe Leu Val Arg Asp Ala Ser Thr Lys Met His Gly Asp Tyr Thr
            355                 360                 365

Leu Thr Leu Arg Lys Gly Gly Asn Asn Lys Leu Ile Lys Ile Phe His
            370                 375                 380

Arg Asp Gly Lys Tyr Gly Phe Ser Asp Pro Leu Thr Phe Asn Ser Val
385                 390                 395                 400

Val Glu Leu Ile Asn His Tyr Arg Asn Glu Ser Leu Ala Gln Tyr Asn
                405                 410                 415

Pro Lys Leu Asp Val Lys Leu Leu Tyr Pro Val Ser Lys Tyr Gln Gln
            420                 425                 430

Asp Gln Val Val Lys Glu Asp Asn Ile Glu Ala Val Gly Lys Lys Leu
            435                 440                 445

His Glu Tyr Asn Thr Gln Phe Gln Glu Lys Ser Arg Glu Tyr Asp Arg
            450                 455                 460

Leu Tyr Glu Glu Tyr Thr Arg Thr Ser Gln Glu Ile Gln Met Lys Arg
465                 470                 475                 480

Thr Ala Ile Glu Ala Phe Asn Glu Thr Ile Lys Ile Phe Glu Glu Gln
                    485                 490                 495

Cys Gln Thr Gln Glu Arg Tyr Ser Lys Glu Tyr Ile Gly Lys Phe Lys
                500                 505                 510

Arg Glu Gly Asn Glu Lys Glu Ile Gln Arg Ile Met His Asn His Asp
            515                 520                 525

Lys Leu Lys Ser Arg Ile Ser Glu Ile Ile Asp Ser Arg Arg Arg Leu
            530                 535                 540

Glu Glu Asp Leu Lys Lys Gln Ala Ala Tyr Arg Glu Ile Asp Lys
545                 550                 555                 560

Arg Met Asn Ser Ile Lys Pro Asp Leu Ile Gln Leu Arg Lys Thr Arg
                    565                 570                 575

Asp Gln Tyr Leu Met Trp Leu Thr Gln Lys Gly Val Arg Gln Lys Lys
                580                 585                 590

Leu Asn Glu Trp Leu Gly Asn Glu Asn Thr Glu Asp Gln Tyr Ser Leu
            595                 600                 605

Val Glu Asp Asp Glu Asp Leu Pro His His Asp Lys Thr Trp Asn Val
            610                 615                 620

Gly Ser Ser Asn Arg Asn Lys Ala Glu Asn Leu Leu Arg Gly Lys Arg
625                 630                 635                 640

Asp Gly Thr Phe Leu Val Arg Glu Ser Ser Lys Gln Gly Cys Tyr Ala
                    645                 650                 655

Cys Ser Val Val Val Asp Gly Glu Val Lys His Cys Val Ile Asn Lys
                660                 665                 670

Thr Ala Thr Gly Tyr Gly Phe Ala Glu Pro Tyr Asn Leu Tyr Ser Ser
            675                 680                 685
```

```
Leu Lys Glu Leu Val Leu His Tyr Gln His Thr Ser Leu Val Gln His
    690             695             700

Asn Asp Ser Leu Asn Val Thr Leu Ala Tyr Pro Val Tyr Ala Gln Gln
705             710             715             720

Arg Arg (2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Ser Tyr Pro Tyr Asp Val Pro Asp Tyr Ala Ser Leu Gly Gly Pro Ser
1               5                   10                  15
```